United States Patent [19]
Kimura et al.

[11] Patent Number: 5,519,016
[45] Date of Patent: May 21, 1996

[54] ARYL GROUP- OR AROMATIC HETEROCYCLIC GROUP-SUBSTITUTED AMINOQUINOLONE DERIVATIVES AND ANTI-HIV AGENT

[75] Inventors: Tomio Kimura; Tetsushi Katsube, both of Ube, Japan

[73] Assignee: Ube Industries, Ltd., Ube, Japan

[21] Appl. No.: 341,295

[22] Filed: Nov. 15, 1994

Related U.S. Application Data

[63] Continuation of Ser. No. 66,985, May 25, 1993, abandoned.

[30] Foreign Application Priority Data

May 27, 1992 [JP] Japan .................... 4-158912

[51] Int. Cl.$^6$ .................... A61K 31/47; A61K 31/495; C07D 215/227; C07D 215/233
[52] U.S. Cl. .................... 514/212; 514/218; 514/233.5; 514/234.5; 514/254; 514/300; 514/312; 544/121; 544/122; 544/295; 544/363; 540/575; 540/597; 546/122; 546/123; 546/153; 546/156
[58] Field of Search .................... 544/295, 363, 544/121, 122, 123, 153, 156; 540/575, 597; 514/233.5, 234.5, 254, 212, 218, 300, 312

[56] References Cited

U.S. PATENT DOCUMENTS

| | | | |
|---|---|---|---|
| 4,840,956 | 6/1989 | Domagala et al. | 514/312 |
| 4,880,806 | 11/1989 | Ueda et al. | 514/249 |
| 5,086,649 | 2/1992 | Kise et al. | 514/210 |
| 5,210,193 | 5/1993 | Sum et al. | 544/360 |
| 5,217,972 | 6/1993 | Grohe et al. | 514/254 |

FOREIGN PATENT DOCUMENTS

| | | |
|---|---|---|
| 0470252 | 11/1990 | European Pat. Off. . |
| 422485 | 4/1991 | European Pat. Off. . |
| WO92/21659 | 12/1992 | WIPO . |

OTHER PUBLICATIONS

Elrod et al., Journal of Chromatography, 519(1) 125–136, 1990.
Ruprecht et al., AIDS Research and Human Retroviruses, 8(6) 1992 pp. 997–1011.
"AIDS, The Unanswered Questions", Science 260, 1253–1293, J. Benditt, ed., 28 May 1993.
Chemical Abstracts, vol. 114, 1991 Abstract No. 247292, "Preparation of 4-oxo-3-quinolonecarboxylic acids and 4-oxo-1,8 naphthyridine-3-carboxylic acids as antiviral agents" of JP 02,264,724.
Junko Nozaki-Renard et al, "A Fluoroquinolone (DR-3355) protects human lymphocyte cell lines from HIV-1-induced cytotoxicity", (1990), vol. 4, No. 1, pp. 1283–1286, AIDS.

Primary Examiner—Mukund J. Shah
Assistant Examiner—Matthew V. Grumbling
Attorney, Agent, or Firm—Frishauf, Holtz, Goodman, Langer & Chick

[57] ABSTRACT

Disclosed are an aryl group- or heterocyclic group-substituted aminoquinolone compound represented by the formula (Ia), (Ib) or (Ic):

wherein each of the substitutents are defined in the specification, or a salt of the compound, and an AIDS curing agent containing the same as an effective ingredient.

23 Claims, No Drawings

ARYL GROUP- OR AROMATIC HETEROCYCLIC GROUP-SUBSTITUTED AMINOQUINOLONE DERIVATIVES AND ANTI-HIV AGENT

This application is a Continuation, of application Ser. No. 08/066,985, filed May 25, 1993, now abandoned.

BACKGROUND OF THE INVENTION

The present invention relates to derivatives of aminoquinolone, and uses therefor.

AIDS (Acquired Immuno-deficiency Syndrome) is now generally accepted as being caused by the Human Immunodeficiency Virus (HIV).

The aetiology of AIDS is not yet precisely known, but it is known that HIV mainly infects $CD_4$ lymphocytes, generally of the class of helper/inducer cells. Lymphocyte numbers gradually decrease, and this eventually leads to severe cellular immunodeficiency.

Very considerable research has been put into finding a cure for AIDS, but the development of a vaccine has proven extremely difficult. Accordingly, other avenues have also been pursued. One such avenue is the development of antiviral agents.

An antiviral agent currently on the market for the treatment of AIDS is AZT (Azidothymidine). The method of action of AZT is to inhibit the inherent reverse transcriptase of HIV, thus retarding or stopping reproduction of the virus. However, such a treatment can, at the best, only prolong life expectancy, and cannot cure AIDS completely. Other antiviral agents which have been developed act in a similar fashion.

Such inhibitory agents are also associated with side effects, such as disorders of the bone marrow and digestive system, and it has also been found that tolerance, or even total resistance, can be induced in the virus with a high frequency. Such resistant viruses can be generated even in patients receiving long-term therapy.

In order to overcome the above problems, it would be highly desirable to develop new antiviral agents which could be used either alone, or in combination therapy with known agents.

Anti-HIV activity has recently been reported for the compound DR-3355, which is an optical isomer (S-isomer) of Ofloxacin, a synthetic anti-bacterial agent. Ofloxacin has a quinolone skeleton [J. Nozaki, Renard et l., AIDS (1990), 4, p. 1283]. Attempts by the present inventors to reproduce the antiviral activity of DR-3355, using the method of R. Pauwel, et al., (infra), have failed.

WO-A-90-13542 discloses the anti-HIV activity of Norfloxacin, Enoxacin, Ciprofloxacin, Lomefloxacin, Difloxacin and Tosufloxacin but, again, these compounds demonstrate little or no anti-HIV activity when tested by the Pauwel method. These compounds also possess a quinolone skeleton.

SUMMARY OF THE INVENTION

We have now discovered a series of new quinolone derivatives which, whilst exhibiting considerably weaker antibacterial activity than those quinolone derivatives described above, exhibit very considerably enhanced anti-HIV activity. The new compounds disclosed herein have increased lipophilicity, and possess a diamine substituent which is, itself, further substituted by an aromatic group, such as an aryl group or an aromatic heterocyclic group. The compounds of the invention are both capable of inhibiting HIV replication and inhibiting the cytopathic effect (CPE) of HIV, and so are useful as agents to inhibit HIV replication and as anti-AIDS agents.

In a first aspect, the present invention provides a compound of the general formula (Ia), (Ib) or (Ic):

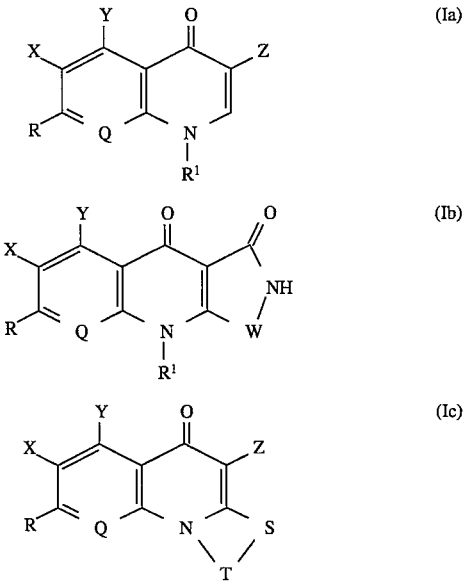

in which

X represents a hydrogen atom or a halogen atom;

Y represents a hydrogen atom, a halogen atom, a lower alkyl group, an amino group, or an amino group substituted by one or two groups selected from lower alkyl and aralkyl groups;

Z represents a carboxyl group or a 5-tetrazolyl group;

Q represents a nitrogen atom or a group of formula (d):

where $R^2$ represents a hydrogen atom, a halogen atom, a lower alkoxy group, a lower alkoxy group substituted by one or more halogen atoms, a lower alkyl group, a lower alkyl group substituted by one or more halogen atoms;

W represents an oxygen atom or a sulfur atom;

T represents a $C_{1-4}$ alkylene group or a $C_{2-4}$ alkenylene group, said groups optionally being substituted by a lower alkyl group;

$R^1$ represents: a hydrogen atom; a lower alkenyl group which may optionally be substituted by one or more halogen atoms; a lower alkynyl group; an amino group which may optionally be substituted by one or more lower alkyl groups; a cycloalkyl group which may optionally be substituted by at least one halogen atom; a lower alkoxy group; an aryl group which may optionally be substituted by at least one substituent $R^0$ as defined below; a 5- or 6-membered aromatic heteromonocyclic group having one or two heteroatoms selected from N, O and S, said ring optionally being substituted by at least one substituent $R^0$ as defined below; a fused aromatic group consisting of a benzene ring fused with a 5- or 6-membered aromatic heteromonocyclic group as defined above, said fused group optionally being substituted by at least one substituent $R^0$ as defined below; a lower alkyl group; or a lower alkyl group substituted by at least one substituent selected from halogen atoms, hydroxyl groups, carboxyl groups, alkanoyloxy groups, cycloalkyl groups, aryl groups which may optionally be substituted by at least one substituent $R^0$ as defined below, 5- or 6-membered aromatic heteromonocyclic groups having one or two heteroatoms selected from N, O and S, said ring optionally being substituted by at least one substituent $R^0$ as defined below, fused aromatic groups as defined above, said fused group optionally being substituted by at least one substituent $R^0$ as defined below, or an amino group represented by the formula (e):

(e)

wherein $R^9$ and $R^{10}$ separately represent a hydrogen atom or a lower alkyl group, or $R^9$ and $R^{10}$, together with the nitrogen atom to which they are attached, form a 3- to 7-membered saturated monocyclic group comprising at least one further heteroatom selected from N, O and S, or when Q is a group of formula (d), then $R^1$ and $R^2$ may together represent a group of formula (f):

(f)

wherein A represents a hydrogen atom, or a lower alkyl group which may optionally be substituted by at least one substituent selected from halogen atoms, hydroxy and lower alkoxy groups; G represents a nitrogen atom or a group of formula (g):

(g)

$G^1$ represents a methylene group, a carbonyl group, an oxygen atom, a sulfur atom or a group of formula —N($R^{11}$)—, where $R^{11}$ represents a hydrogen atom or a lower alkyl group; and p =0 or 1;

R represents a group of formula (h) or (i):

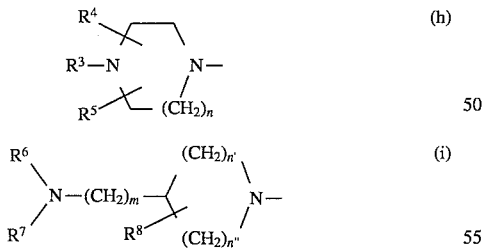
(h)

(i)

where $R^3$ and $R^6$ each represents an aryl group which may optionally be substituted by at least one substituent $R^0$ as defined below; a 5- or 6-membered aromatic heteromonocyclic group having one or two heteroatoms selected from N, O and S, said ring optionally being substituted by at least one substituent $R^0$ as defined below; a fused aromatic group consisting of a benzene ring fused with a 5- or 6-membered aromatic heteromonocyclic group as defined above, said fused group optionally being substituted by at least one substituent $R^0$ as defined below;

$R^4$, $R^5$ and $R^7$ may be the same or different, and each represents a hydrogen atom or a lower alkyl group;

$R^8$ represents a hydrogen atom, a lower alkyl group, a hydroxy group or a lower alkoxy group;

n =1 or 2;

m =0 or 1;

n =1 or 2; and n =1, 2, 3 or 4;

and substituent $R^0$ are selected from halogen atoms, nitro groups, hydroxy groups, lower alkyl groups which may optionally be substituted with at least one halogen atom, lower alkoxy groups, and amino groups which may optionally be substituted with one or two lower alkyl groups, and when there are two or more substituents $R^0$, each may be the same or different, or a pharmaceutically acceptable salt or ester thereof and an AIDS curing agent containing the compound represented by the above formula (Ia), (Ib) or (Ic) or an ester thereof as an active ingredient.

DESCRIPTION OF THE PREFERRED EMBODIMENTS

In the following, the present invention is explained in detail.

The compounds represented by the formula (Ia), (Ib) and (Ic) include compounds represented by the formulae (Ia-1), (Ib-1) and (Ic-1) and the formulae (Ia-2), (Ib-2) and (Icshown below.

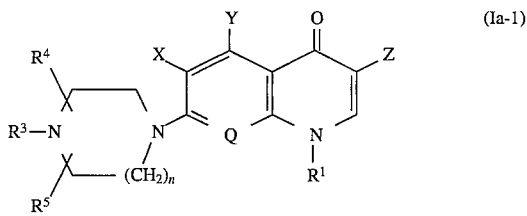
(Ia-1)

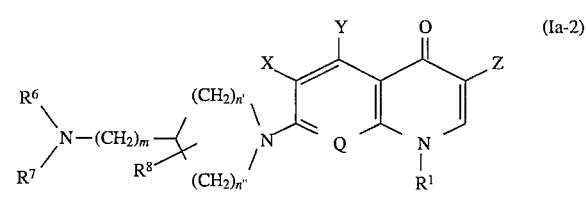
(Ia-2)

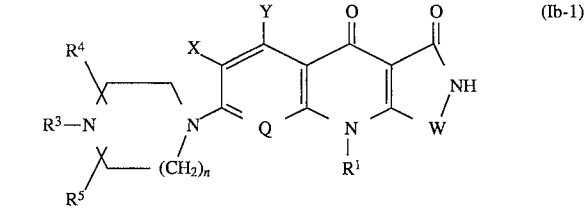
(Ib-1)

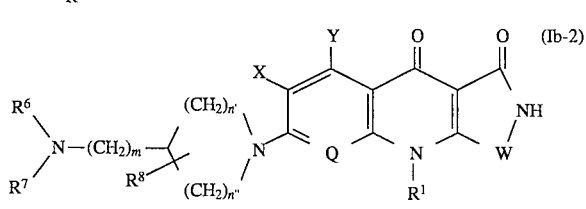
(Ib-2)

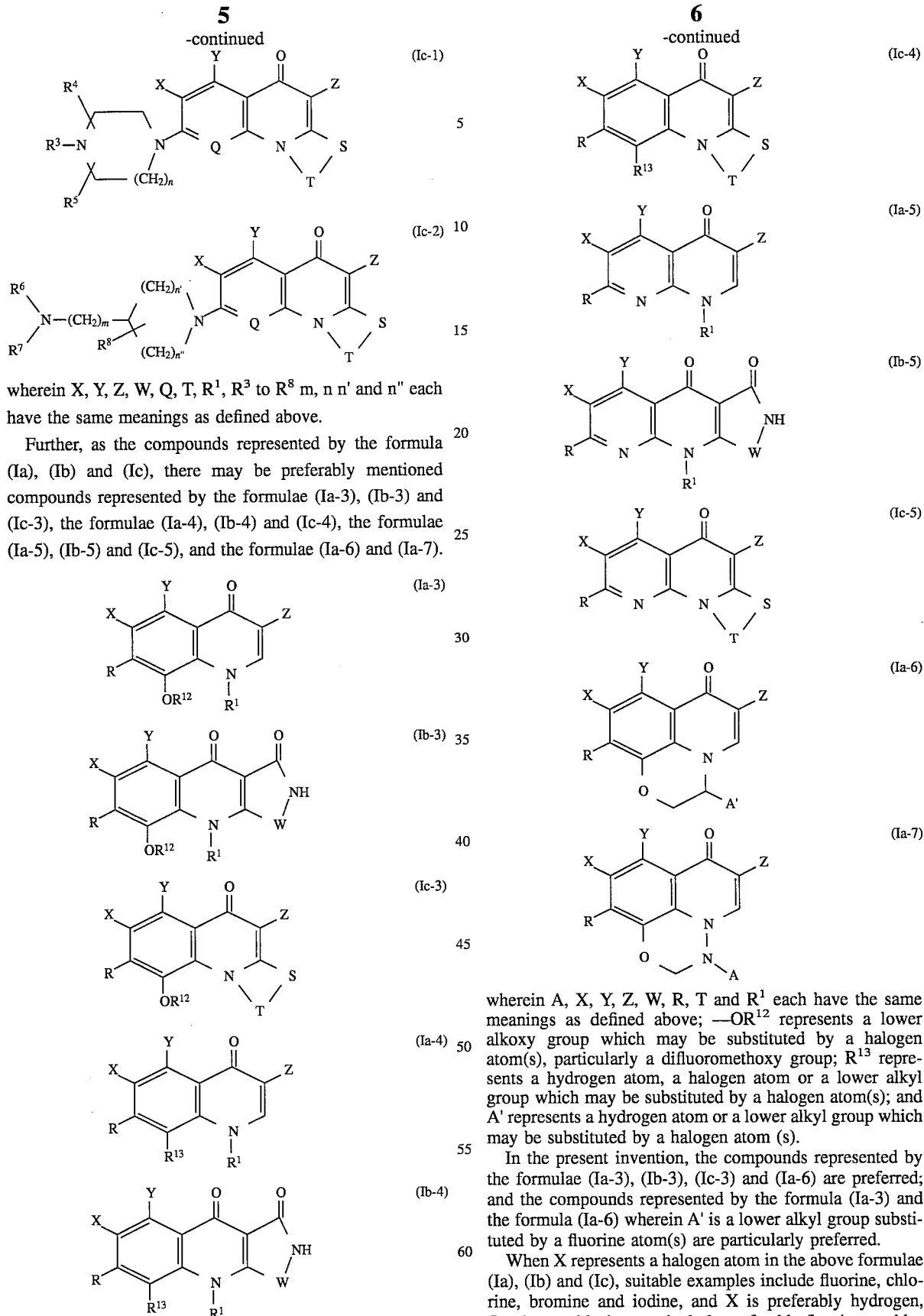

wherein X, Y, Z, W, Q, T, $R^1$, $R^3$ to $R^8$ m, n n' and n" each have the same meanings as defined above.

Further, as the compounds represented by the formula (Ia), (Ib) and (Ic), there may be preferably mentioned compounds represented by the formulae (Ia-3), (Ib-3) and (Ic-3), the formulae (Ia-4), (Ib-4) and (Ic-4), the formulae (Ia-5), (Ib-5) and (Ic-5), and the formulae (Ia-6) and (Ia-7).

wherein A, X, Y, Z, W, R, T and $R^1$ each have the same meanings as defined above; $-OR^{12}$ represents a lower alkoxy group which may be substituted by a halogen atom(s), particularly a difluoromethoxy group; $R^{13}$ represents a hydrogen atom, a halogen atom or a lower alkyl group which may be substituted by a halogen atom(s); and A' represents a hydrogen atom or a lower alkyl group which may be substituted by a halogen atom (s).

In the present invention, the compounds represented by the formulae (Ia-3), (Ib-3), (Ic-3) and (Ia-6) are preferred; and the compounds represented by the formula (Ia-3) and the formula (Ia-6) wherein A' is a lower alkyl group substituted by a fluorine atom(s) are particularly preferred.

When X represents a halogen atom in the above formulae (Ia), (Ib) and (Ic), suitable examples include fluorine, chlorine, bromine and iodine, and X is preferably hydrogen, fluorine or chlorine, particularly preferably fluorine or chlorine, and most preferably fluorine.

Suitable examples of Y in the above formulae (Ia), (Ib) and (Ic) include a hydrogen atom; a halogen atom such as fluorine, chlorine, bromine and iodine; a straight or branched chain $C_1$ to $C_4$ alkyl group such as methyl, ethyl, propyl, isopropyl, butyl and isobutyl; an amino group; a mono-$C_1$ to $C_4$ alkylamino group such as methylamino, ethylamino, propylamino, isopropylamino and butylamino; a di-$C_1$ to $C_4$ alkylamino group such as dimethylamino, diethylamino, dipropylamino, diisopropylamino and dibutylamino; a mono aralkylamino group such as benzylamino and phenylethylamino; and a diaralkylamino group such as dibenzylamino.

The above Y is preferably hydrogen, fluorine, amino, methyl or ethyl, particularly preferably hydrogen, fluorine, amino or methyl, most preferably hydrogen.

Suitable examples of Z in the above formulae (Ia) and (Ic) include a carboxyl group which may be protected or a 5-tetrazolyl group. Where the compound of the present invention is an ester, for example, where Z represents a carboxyl group, then suitable ester groupings include a $C_1$ to $C_4$ alkyl, aralkyl, $C_1$ to $C_4$ alkanoyloxyalkyl, $C_1$ to $C_4$ alkoxycarbonyloxyalkyl, N,N-dialkyl-substituted aminocarbonylalkyl, N,N-dialkyl-substituted aminoalkyl, alkyl substituted by a 5- or 6-membered saturated monocyclic group having one or two hetero atoms selected from N, O and S, and (5-methyl- or 5-phenyl-2-oxo-1,3-dioxolen-4-yl)methyl. The above Z is preferably a carboxyl group which may be protected.

W in the above formula (Ib) is an oxygen atom or a sulfur atom, particularly preferably a sulfur atom.

Suitable examples of T in the above formula (Ic) include a $C_1$ to $C_4$ alkylene group which may be substituted by a $C_1$ to $C_4$ alkyl, such as methylene, ethylidene (—CH(CH$_3$)—), ethylene, trimethylene, propylene and tetramethylene, or a $C_2$ to $C_4$ alkenylene group which may be substituted by a $C_1$ to $C_4$ alkyl, such as —CH=CH— and —C(CH$_3$)=CH—. T is preferably ethylidene, —CH=CH— or —C(CH$_3$)=CH—, particularly preferably ethylidene.

Suitable examples of the halogen atom represented by $R^2$ of the formula (d) represented by Q in the above formulae (Ia), (Ib) and (Ic) include fluorine, chlorine, bromine and iodine, preferably fluorine or chlorine.

Suitable examples of the lower alkyl group which may be substituted by a halogen atom(s) represented by $R^2$ include a $C_1$ to $C_4$ alkyl group such as methyl, ethyl, propyl, isopropyl and butyl, or a fluorine-substituted $C_1$ to $C_4$ lower alkyl group such as fluoromethyl, difluoromethyl, trifluoromethyl, 2-fluoroethyl, 3-fluoropropyl and 4-fluorobutyl, and methyl or trifluoromethyl is preferred.

Suitable examples of the lower alkoxy group which may be substituted by a fluorine atom(s) represented by $R^2$ include a $C_1$ to $C_4$ alkoxy group such as methoxy, ethoxy, propoxy, isopropoxy and butoxy, or a fluorine-substituted $C_1$ to $C_4$ alkoxy group such as fluoromethoxy, difluoromethoxy, trifluoromethoxy, 2-fluoroethoxy, 2- or 3-fluoropropoxy and 4-fluorobutoxy, preferably methoxy, ethoxy, mono-, di- or trifluoromethoxy or 2-fluoroethoxy, particularly preferably methoxy and mono-, di- or trifluoromethoxy, most preferably methoxy or difluoromethoxy.

The above $R^2$ is preferably hydrogen; a halogen atom such as fluorine and chlorine; a lower alkyl group which may be substituted by a halogen atom such as methyl and trifluoromethyl; a lower alkoxy group which may be substituted by a halogen atom such as methoxy, ethoxy, fluoromethoxy, difluoromethoxy, trifluoromethoxy or 2-fluoroethoxy; particularly preferably a methoxy group which may be substituted by a fluorine atom(s). Further, in the formula (Ia), a compound wherein $R^2$ is a methoxy group or a difluoromethoxy group is most preferred.

In the present specification, a lower alkyl/alkoxy group includes no more than 6 carbon atoms, preferably no more than 4, particularly 1, 2 or 3.

In the present invention, the characteristic feature of the compounds represented by the formulae (Ia), (Ib) and (Ic) resides in that R in the formulae is a group represented by the formula (h) or (i) and to the nitrogen atom is bound the above aryl group or the aromatic heterocyclic group of $R^3$ or $R^6$ each of which may be substituted by $R^0$.

In the above formula (h), n is preferably 1. In the formula (i), the sum of n' and n" is preferably 3, 4 or 5 and particularly preferably 3 or 4. m is preferably 0.

In the above formulae (h) and (i), the aryl group represented by $R^3$ or $R^6$ may include phenyl and naphthyl, and the aromatic heteromonocyclic or fused heterocyclic group (hereinafter referred to as an "aromatic heterocyclic group") may include 2-thienyl, 2-furyl, 2-oxazolyl, 2-thiazolyl, 2-imidazolyl, 2-, 3- or 4-pyridyl, 2-, 4- or 5-pyrimidinyl, 2-pyrazinyl, 3-pyridazinyl, 2-benzoxazolyl, 2-benzothiazolyl and 2-benzimidazolyl.

As the substituent $R^0$ substituted on the above aryl or aromatic heterocyclic group, there may be mentioned a halogen atom such as fluorine, chlorine, bromine and iodine; a nitro group; a hydroxyl group; a straight or branched chain $C_1$ to $C_4$ alkyl group such as methyl, ethyl, propyl, isopropyl, butyl, s-butyl, isobutyl and t-butyl; a fluorine-substituted $C_1$ to $C_4$ alkyl group such as mono-, di- or trifluoromethyl, 2-fluoroethyl, 2- or 3-fluoropropyl and 2-, 3or 4-fluorobutyl; a $C_1$ to $C_4$ alkoxy group such as methoxy, ethoxy, propoxy, isopropoxy and butoxy; an amino group, a mono- $C_1$ to $C_4$ alkyl-substituted amino group such as methylamino, ethylamino, propylamino, isopropylamino, butylamino, isobutylamino, s-butylamino and t-butylamino; and a di- $C_1$ to $C_4$ alkyl-substituted amino group such as dimethylamino, diethylamino, dipropylamino, diisopropylamino, dibutylamino, diisobutylamino and ethyl(methyl)amino.

As the above $R^3$ and $R^6$ the aromatic heterocyclic group which may be substituted by $R^0$ as mentioned above is preferred, and those wherein R is represented by the formula (h) and $R^3$ in the formula (h) is an aromatic heterocyclic group which may be substituted by $R^0$ are particularly preferred. Among them, those in which $R^3$ is a 5- or 6-membered heteromonocyclic group having 1 or 2 nitrogen atom, which may be substituted by $R^0$, are particularly preferred. Further preferred are those in which $R^3$ is a pyridyl group, pyrazinyl group or pyrimidinyl group which may be substituted by $R^0$ and $R^3$ is particularly preferably 2-pyrimidinyl group.

Also, a compound wherein R is represented by the formula (h) and $R^3$ in the formula (h) is a phenyl group substituted by $R^0$ as mentioned above is preferred.

As the above $R^3$, there may be preferably mentioned phenyl; 2-pyridyl; 2-pyrazinyl; 2- or 4-pyrimidinyl; dimethoxy-2-pyrimidinyl; 2-thiazolyl; 2-benzoxazolyl; 2-benzothiazolyl; a phenyl substituted by fluorine, chlorine, methoxy, nitro, trifluoromethyl, amino or dimethylamino at 2-, 3- or 4-position; a methoxy-, amino- or nitro-substituted 2-pyridyl; and a chlorine-, methyl- or ethyl-substituted 2- or 4-pyrimidinyl; particularly preferred are phenyl; 2-pyridyl; 2-pyrazinyl; 2- or 4-pyrimidinyl; 2-thiazolyl; a phenyl substituted by fluorine, chlorine, methoxy, nitro, trifluoromethyl, amino or dimethylamino at 2-, 3- or 4-position; a methoxy- or nitro-substituted 2-pyridyl; or a chlorine-, methyl- or ethyl-substituted 2- or 4-pyrimidinyl.

R is most preferably a 4-(2-pyrimidinyl)piperazin-1-yl.

In the above formulae (h) and (i), the lower alkyl group represented by $R^4$ $R^5$ or $R^7$ may include a $C_1$ to $C_4$ alkyl group such as methyl, ethyl, propyl, isopropyl, butyl, isobutyl and t-butyl, preferably a methyl or an ethyl.

In the above formula (i), the lower alkyl group represented by $R^8$ may include a straight or branched chain $C_1$ to $C_4$ alkyl group such as methyl, ethyl, propyl, isopropyl, butyl, isobutyl and t-butyl, preferably methyl, ethyl, propyl or isopropyl, more preferably methyl or ethyl.

In the above formula (i), the lower alkoxy group represented by $R^8$ may include a $C_1$ to $C_4$ alkoxy group such as methoxy, ethoxy, propoxy, isopropoxy and butoxy, preferably methoxy, ethoxy or propoxy.

The above $R^4$ $R^5$ and $R^7$ are preferably a hydrogen atom methyl, ethyl, propyl or isopropyl, particularly preferably a hydrogen atom, methyl or ethyl.

The above $R^8$ is preferably a hydrogen atom, a hydroxy group, methyl, ethyl, propyl, isopropyl, methoxy, ethoxy or propoxy, particularly preferably a hydrogen atom, a hydroxy group, methyl, ethyl, methoxy or ethoxy.

In the above formulae (Ia) and (Ib), the lower alkyl group and lower alkoxy group represented by $R^1$ may include the same straight or branched chain $C_1$ to $C_4$ alkyl group mentioned as the lower alkyl group represented by the above $R^8$ and the same $C_1$ to $C_4$ alkoxy group mentioned as the lower alkoxy group represented by the above $R^8$.

As the lower alkyl group having a substituent(s) represented by the above $R^1$, there may be mentioned a hydroxy $C_1$ to $C_4$ alkyl group such as 2-hydroxyethyl, 2- or 3-hydroxypropyl, 2-, 3- or 4-hydroxybutyl; a carboxyl $C_1$ to $C_4$ alkyl group such as carboxymethyl, 1- or 2-carboxyethyl, 1- or 3-carboxypropyl, 1-carboxybutyl and 1-carboxy-2-hydroxyethyl; a halogeno $C_1$ to $C_4$ alkyl group such as fluoro-, chloro-, bromo- or iodomethyl, 2-(fluoro-, chloro-, bromo- or iodo)ethyl, 2- or 3-(fluoro-, chloro-, bromo- or iodo)propyl, 2-, 3- or 4-(fluoro-, chloro-, bromo- or iodo)butyl, difluoromethyl, trifluoromethyl and 2,2,2-trifluoroethyl; a $C_3$ to $C_6$ cycloalkyl $C_1$ to $C_4$ alkyl group such as cyclopropylmethyl, cyclobutylmethyl, cyclopentylmethyl, cyclohexylmethyl, cyclopropylethyl, cyclopropylpropyl and cyclopropylbutyl; a $C_1$ to $C_4$ alkanoyloxy $C_1$ to $C_4$ alkyl group such as 2-acetoxyethyl, 2- or 3-acetoxypropyl, 2-, 3- or 4-acetoxybutyl, 2-propionyloxyethyl and 2-butyryloxyethyl; a $C_1$ to $C_4$ alkyl group substituted by the same aryl group or aromatic heterocyclic group as mentioned as examples of $R^3$ and $R^6$ in the above formulae (h) and (i) , or the $C_1$ to $C_4$ alkyl group substituted by a substituent represented by the above formula (e).

The lower alkyl group represented by $R^9$ or $R^{10}$ in the above formula (e) may include the same straight or branched chain $C_1$ to $C_4$ alkyl group as mentioned as the lower alkyl group represented by the above $R^8$, and the saturated heteromonocyclic group formed by $R^9$ and $R^{10}$ in combination in the above formula (e) may include each group of aziridino, azetidino, pyrrolidino, piperidino, morpholino, thiomorpholino and piperazino.

Suitable examples of the mono- or di-lower alkyl-substituted amino group represented by the above $R^1$ include a mono-$C_1$ to $C_4$ alkylamino group such as methylamino, ethylamino, propylamino, isopropylamino and butylamino, and a di-$C_1$ to $C_4$ alkylamino group such as dimethylamino, diethylamino, dipropylamino, diisopropylamino and dibutylamino.

Suitable examples of the cycloalkyl group which may be substituted by a halogen represented by the above $R^1$ include a $C_3$ to $C_6$ cycloalkyl group such as cyclopropyl, cyclobutyl, cyclopentyl and cyclohexyl; and a halogeno-$C_3$ to $C_6$ cycloalkyl group such as 2-fluoro-, 2-chloro- or 2-bromocyclopropyl, 2,2-difluorocyclopropyl, 2-chloro-2-fluorocyclopropyl, 2-fluorocyclobutyl, 2-fluorocyclopentyl and 2-fluorocyclohexyl.

Suitable examples of the lower alkenyl group which may be substituted by a halogen represented by the above $R^1$ include a $C_2$ to $C_5$ lower alkenyl group such as vinyl, 1- or 2-propenyl, 1-, 2- or 3-butenyl and 3,3-dimethyl-2-propenyl; and a halogeno-$C_2$ to $C_4$ lower alkenyl group such as 3,3-dichloro-2-propenyl, 2,3-dichloro-2-propenyl and 4-chloro-3-butenyl.

Suitable examples of the lower alkynyl group represented by the above $R^1$ include a $C_2$ to $C_4$ lower alkynyl group such as ethynyl, 1- or 2-propynyl and 2-butynyl.

Suitable examples of $R^1$ as mentioned above preferably include hydrogen atom; methyl, ethyl, propyl, isopropyl, butyl or t-butyl as the lower alkyl group; 2-hydroxyethyl, 2- or 3-hydroxypropyl, carboxymethyl, 1- or 2-carboxyethyl, fluoromethyl, 2-fluoroethyl, 2-chloroethyl, 3-fluoropropyl, 3-chloropropyl, difluoromethyl, trifluoromethyl, 2,2,2-trifluoroethyl, cyclopropylmethyl, 2-acetoxyethyl, 2- or 3-acetoxypropyl, phenylmethyl, 1- or 2-phenylethyl, naphthylmethyl, 2-, 3- or 4-fluorophenylmethyl, 2,4-, 3,4- or 2,6-difluorophenylmethyl, 2-, 3- or 4-methylphenylmethyl, 2-, 3- or 4-chlorophenylmethyl, 2-, 3- or 4-methoxyphenylmethyl, 2-thienylmethyl, 2-furylmethyl, 2-pyridylmethyl, 2-pyrimidinylmethyl, 2-aminoethyl, 2-methylaminoethyl, 2-dimethylaminoethyl, 2-morpholinoethyl or 2-piperidinoethyl as the lower alkyl group having a substituent(s); an amino group; methylamino, ethylamino or dimethylamino as the amino group substituted by a lower alkyl; methoxy, ethoxy or propoxy as the lower alkoxy group; cyclopropyl, cyclobutyl, cyclopentyl or 2-fluorocyclopropyl as the cycloalkyl group which may be substituted by a halogen; phenyl, naphthyl, 2-, 3- or 4-fluorophenyl, 2-, 3- or 4-chlorophenyl, 2,4-, 3,4- or 2,6-difluorophenyl or 2-, 3- or 4-methylphenyl as the aryl group; 2-thiazolyl, 2-oxazolyl, 2-, 3or 4-pyridyl, 2-, 4- or 5-pyrimidinyl, 2-benzoxazolyl or 2-benzothiazolyl as the aromatic hetero cyclic group; vinyl, 2-propenyl, 3,3-dimethylpropenyl or 3,3-dichloropropenyl as the lower alkenyl group which may be substituted by a halogen; and ethynyl or 2-propynyl as the lower alkynyl group.

As to the above $R^1$, it is particularly preferred that the lower alkyl group is methyl, ethyl, propyl or isopropyl; the lower alkyl group having a substituent(s) is 2-hydroxyethyl, carboxymethyl, 2-fluoroethyl, 2-acetoxyethyl, phenylmethyl, phenylethyl, 2-pyridylmethyl, 2-dimethylaminoethyl or 2-morpholinoethyl; an amino group; the amino group substituted by a lower alkyl is methylamino; the lower alkoxy group is methoxy; the cycloalkyl group which may be substituted by a halogen is cyclopropyl or 2-fluorocyclopropyl; the aryl group which may be substituted by a halogen(s) is phenyl, 2-, 3- or 4-fluorophenyl or 2,4-difluorophenyl; the lower alkenyl group which may be substituted by a halogen is vinyl or 2-propenyl; and the lower alkynyl group is 2-propynyl.

When the bond represented by the formula (f) is formed by $R^1$ in the above formulae (Ia) and (Ib), and $R^2$ in combination, A in the formula (f) may include a hydrogen atom; a $C_1$ to $C_4$ alkyl group such as methyl, ethyl, propyl, isopropyl and butyl; a halogeno-$C_1$ to $C_4$ alkyl group such as fluoromethyl, chloromethyl, difluoromethyl, trifluoromethyl, 2-fluoroethyl, 2-chloroethyl, 2-bromoethyl, 2- or 3-fluoropropyl and 2-, 3- or 4-fluorobutyl; a hydroxy-$C_1$ to $C_4$ alkyl group such as hydroxymethyl, 2-hydroxyethyl, 3-hydroxypropyl and 4-hydroxybutyl; and a $C_1$ to $C_4$ alkoxy-$C_1$ to $C_4$ alkyl group such as methoxymethyl, ethoxymethyl, propoxymethyl, butoxymethyl, methoxyethyl, methoxypropyl and methoxybutyl. In the formula (f), G may include a nitrogen atom or a trivalent group represented by the formula (g), $G^1$ may include a methylene group, a carbonyl group, an oxygen atom, a sulfur atom and —N($R^{11}$)— where $R^{11}$ represents a hydrogen atom, a $C_1$ to $C_4$ alkyl group such as methyl, ethyl, propyl and butyl; and p is 0 or 1.

In the above formula (f), A is preferably a hydrogen atom, a lower alkyl group which may be substituted by a halogen, such as methyl, ethyl, propyl, isopropyl and fluoromethyl, particularly preferably methyl and fluoromethyl. As G, a group represented by the formula (g) is preferred. Also, as $G^1$, it is preferably an oxygen atom or a sulfur atom, particularly suitably an oxygen atom. p is most preferably 1.

When the above formula (Ia), (Ib) or (Ic) has a carboxyl group in the molecule (i.e. as Z or $R^1$), such a carboxyl group may be protected. As such a protective group, there may be mentioned a group which is easily deprotected in vivo to be converted into a carboxyl group, including a $C_1$ to $C_4$ alkyl group such as methyl, ethyl, propyl, isopropyl, butyl and isobutyl; an aralkyl group such as benzyl and phenylethyl; a $C_1$ to $C_4$ alkanoyloxyalkyl group such as acetoxymethyl and pivaloyloxymethyl; a $C_1$ to $C_4$ alkoxycarbonyloxyalkyl group such as 1-(ethoxycarbonyloxy)ethyl and 1-(isopropoxycarbonyloxy)ethyl; an N,N-dialkyl-substituted aminocarbonylalkyl group such as N,N-dimethylaminocarbonylmethyl; and N,N-dialkyl-substituted aminoalkyl group such as 2-(N,N-dimethylamino)ethyl; an alkyl group substituted by a 5- or 6-membered saturated heteromonocyclic group having one or two hetero atoms selected from N, O and S such as 2-morpholinoethyl, 2-piperidinoethyl and 2-(4-methylpiperidino)ethyl; or a (5-methyl- (or 5-phenyl)-2-oxo-1,3-dioxolen-4-yl)methyl group.

In the compounds represented by the above formulae (Ia) and (Ib), when $R^1$ is a hydrogen atom, tautomers shown by the following formulae can exist, and all of these tautomers are included in the present invention.

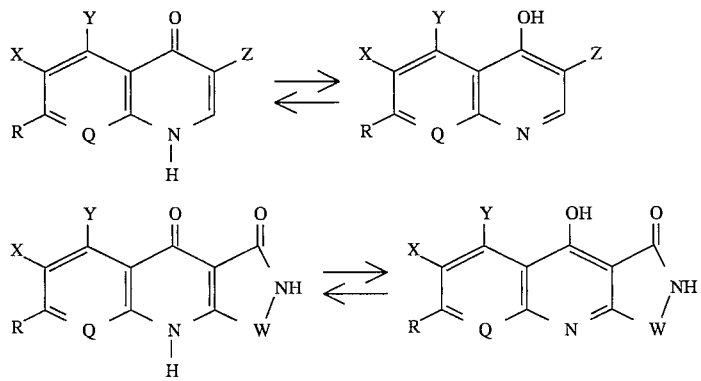

In the present invention, the compound represented by the above formula (Ia), (Ib) or (Ic) can be made into a pharmaceutically acceptable salt, if necessary.

Such a salt may include an acid addition salt of a mineral acid such as a hydrochloride, a hydrobromide, a hydroiodide, a sulfate and a phosphate; an acid addition salt of an organic acid such as a methanesulfonate, an ethanesulfonate, a benzenesulfonate, a p-toluenesulfonate, an oxalate, a maleate, a fumarate, a tartarate and a citrate; or a metal salt of a carboxylic acid such as a sodium salt, a potassium salt, a calcium salt, a magnesium salt, a manganese salt, an iron salt and an aluminum salt.

The compounds of the above formula (Ia), (Ib) or (Ic) of the present invention can exist as a hydrate.

Compounds represented by the above formula (Ia), (Ib) or (Ic) are exemplified in Tables 1 to 20 below.

TABLE 1

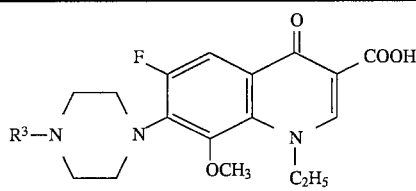

| $R^3$ | $R^3$ |
|---|---|
| Phenyl | 2-Oxazolyl |
| 2-Fluorophenyl | 2-Thiazolyl |
| 3-Fluorophenyl | 2-Imidazolyl |
| 4-Fluorophenyl | 2-Pyridyl |
| 2-Chlorophenyl | 6-Methoxy-2-pyridyl |
| 3-Chlorophenyl | 3-Nitro-2-pyridyl |
| 4-Chlorophenyl | 3-Amino-2-pyridyl |
| 2-Methoxyphenyl | 3-Methylamino-2-pyridyl |
| 3-Methoxyphenyl | 3-Ethylamino-2-pyridyl |
| 4-Methoxyphenyl | 3-Fluoro-2-pyridyl |
| 2-Nitrophenyl | 3-Pyridyl |
| 3-Nitrophenyl | 4-Pyridyl |
| 4-Nitrophenyl | 2-Benzoxazolyl |
| 2-Aminophenyl | 5-Chloro-2-benzoxazolyl |
| 3-Aminophenyl | 2-Benzothiazolyl |
| 4-Aminophenyl | 5-Methyl-2-benzothiazolyl |
| 2-Dimethylaminophenyl | 2-Benzimidazolyl |
| 3-Dimethylaminophenyl | 2-Pyrimidinyl |
| 4-Dimethylaminophenyl | 5-Chloro-2-pyrimidinyl |
| 2-Trifluoromethylphenyl | 4-Methoxy-2-pyrimidinyl |
| 3-Trifluoromethylphenyl | 4,6-Dimethoxy-2-pyrimidinyl |
| 4-Trifluoromethylphenyl | 4-Pyrimidinyl |
| 2,4-Difluorophenyl | 5-Chloro-6-methyl-4-pyrimidinyl |
| | 3-Pyridazinyl |
| | 6-Chloro-3-pyridazinyl |
| | 2-Pyrazinyl |

TABLE 2

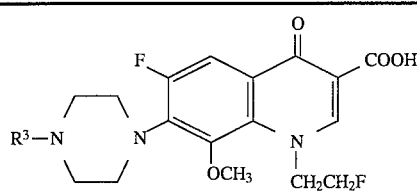

| $R^3$ | $R^3$ |
|---|---|
| Phenyl | 2-Oxazolyl |

TABLE 2-continued

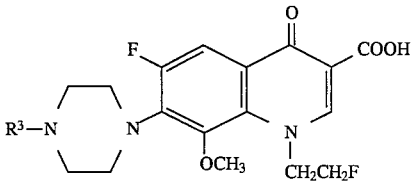

| R³ | R³ |
|---|---|
| 2-Fluorophenyl | 2-Thiazolyl |
| 3-Fluorophenyl | 2-Imidazolyl |
| 4-Fluorophenyl | 2-Pyridyl |
| 2-Chlorophenyl | 6-Methoxy-2-pyridyl |
| 3-Chlorophenyl | 3-Nitro-2-pyridyl |
| 4-Chlorophenyl | 3-Amino-2-pyridyl |
| 2-Methoxyphenyl | 3-Methylamino-2-pyridyl |
| 3-Methoxyphenyl | 3-Ethylamino-2-pyridyl |
| 4-Methoxyphenyl | 3-Fluoro-2-pyridyl |
| 2-Nitrophenyl | 3-Pyridyl |
| 3-Nitrophenyl | 4-Pyridyl |
| 4-Nitrophenyl | 2-Benzoxazolyl |
| 2-Aminophenyl | 5-Chloro-2-benzoxazolyl |
| 3-Aminophenyl | 2-Benzothiazolyl |
| 4-Aminophenyl | 5-Methyl-2-benzothiazolyl |
| 2-Dimethylaminophenyl | 2-Benzimidazolyl |
| 3-Dimethylaminophenyl | 2-Pyrimidinyl |
| 4-Dimethylaminophenyl | 5-Chloro-2-pyrimidinyl |
| 2-Trifluoromethylphenyl | 4-Methoxy-2-pyrimidinyl |
| 3-Trifluoromethylphenyl | 4,6-Dimethoxy-2-pyrimidinyl |
| 4-Trifluoromethylphenyl | 4-Pyrimidinyl |
| 2,4-Difluorophenyl | 5-Chloro-6-methyl-4-pyrimidinyl |
|  | 3-Pyridazinyl |
|  | 6-Chloro-3-pyridazinyl |
|  | 2-Pyrazinyl |

TABLE 3

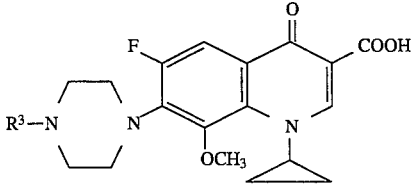

| R³ | R³ |
|---|---|
| Phenyl | 2-Oxazolyl |
| 2-Fluorophenyl | 2-Thiazolyl |
| 3-Fluorophenyl | 2-Imidazolyl |
| 4-Fluorophenyl | 2-Pyridyl |
| 2-Chlorophenyl | 6-Methoxy-2-pyridyl |
| 3-Chlorophenyl | 3-Nitro-2-pyridyl |
| 4-Chlorophenyl | 3-Amino-2-pyridyl |
| 2-Methoxyphenyl | 3-Methylamino-2-pyridyl |
| 3-Methoxyphenyl | 3-Ethylamino-2-pyridyl |
| 4-Methoxyphenyl | 3-Fluoro-2-pyridyl |
| 2-Nitrophenyl | 3-Pyridyl |
| 3-Nitrophenyl | 4-Pyridyl |
| 4-Nitrophenyl | 2-Benzoxazolyl |
| 2-Aminophenyl | 5-Chloro-2-benzoxazolyl |
| 3-Aminophenyl | 2-Benzothiazolyl |
| 4-Aminophenyl | 5-Methyl-2-benzothiazolyl |
| 2-Dimethylaminophenyl | 2-Benzimidazolyl |
| 3-Dimethylaminophenyl | 2-Pyrimidinyl |
| 4-Dimethylaminophenyl | 5-Chloro-2-pyrimidinyl |
| 2-Trifluoromethylphenyl | 4-Methoxy-2-pyrimidinyl |
| 3-Trifluoromethylphenyl | 4,6-Dimethoxy-2-pyrimidinyl |
| 4-Trifluoromethylphenyl | 4-Pyrimidinyl |
| 2,4-Difluorophenyl | 5-Chloro-6-methyl-4-pyrimidinyl |
|  | 3-Pyridazinyl |

TABLE 3-continued

| R³ | R³ |
|---|---|
|  | 6-Chloro-3-pyridazinyl |
|  | 2-Pyrazinyl |

TABLE 4

| R³ | R³ |
|---|---|
| Phenyl | 2-Thiazolyl |
| 2-Fluorophenyl | 2-Imidazolyl |
| 3-Fluorophenyl | 2-Pyridyl |
| 4-Fluorophenyl | 6-Methoxy-2-pyridyl |
| 2-Chlorophenyl | 3-Nitro-2-pyridyl |
| 3-Chlorophenyl | 6-Nitro-2-pyridyl |
| 4-Chlorophenyl | 3-Amino-2-pyridyl |
| 2-Methoxyphenyl | 3-Methylamino-2-pyridyl |
| 3-Methoxyphenyl | 3-Ethylamino-2-pyridyl |
| 4-Methoxyphenyl | 3-Fluoro-2-pyridyl |
| 2-Ethoxyphenyl | 3-Pyridyl |
| 2-Nitrophenyl | 4-Pyridyl |
| 3-Nitrophenyl | 2-Benzoxazolyl |
| 4-Nitrophenyl | 5-Chloro-2-benzoxazolyl |
| 2-Aminophenyl | 2-Benzothiazolyl |
| 3-Aminophenyl | 5-Methyl-2-benzothiazolyl |
| 4-Aminophenyl | 2-Benzimidazolyl |
| 2-Dimethylaminophenyl | 2-Pyrimidinyl |
| 3-Dimethylaminophenyl | 5-Chloro-2-pyrimidinyl |
| 4-Dimethylaminophenyl | 4-Methoxy-2-pyrimidinyl |
| 2-Trifluoromethylphenyl | 4,6-Dimethoxy-2-pyrimidinyl |
| 3-Trifluoromethylphenyl | 4-Pyrimidinyl |
| 4-Trifluoromethylphenyl | 6-Ethyl-4-pyrimidinyl |
| 2,4-Difluorophenyl | 6-Chloro-4-pyrimidinyl |
| 2-Methylphenyl | 5-Chloro-6-methyl-4-pyrimidinyl |
| 3-Methylphenyl | 3-Pyridazinyl |
| 3-Hydroxyphenyl | 6-Chloro-3-pyridazinyl |
| 2-Oxazolyl | 2-Pyrazinyl |

TABLE 5

| R³ | R³ |
|---|---|
| Phenyl | 2-Oxazolyl |
| 2-Fluorophenyl | 2-Thiazolyl |
| 3-Fluorophenyl | 2-Imidazolyl |
| 4-Fluorophenyl | 2-Pyridyl |
| 2-Chlorophenyl | 6-Methoxy-2-pyridyl |

TABLE 5-continued

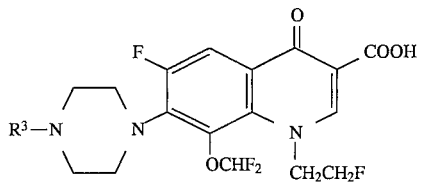

| R³ | R³ |
|---|---|
| 3-Chlorophenyl | 3-Nitro-2-pyridyl |
| 4-Chlorophenyl | 3-Amino-2-pyridyl |
| 2-Methoxyphenyl | 3-Methylamino-2-pyridyl |
| 3-Methoxyphenyl | 3-Ethylamino-2-pyridyl |
| 4-Methoxyphenyl | 3-Fluoro-2-pyridyl |
| 2-Nitrophenyl | 3-Pyridyl |
| 3-Nitrophenyl | 4-Pyridyl |
| 4-Nitrophenyl | 2-Benzoxazolyl |
| 2-Aminophenyl | 5-Chloro-2-benzoxazolyl |
| 3-Aminophenyl | 2-Benzothiazolyl |
| 4-Aminophenyl | 5-Methyl-2-benzothiazolyl |
| 2-Dimethylaminophenyl | 2-Benzimidazolyl |
| 3-Dimethylaminophenyl | 2-Pyrimidinyl |
| 4-Dimethylaminophenyl | 5-Chloro-2-pyrimidinyl |
| 2-Trifluoromethylphenyl | 4-Methoxy-2-pyrimidinyl |
| 3-Trifluoromethylphenyl | 4,6-Dimethoxy-2-pyrimidinyl |
| 4-Trifluoromethylphenyl | 4-Pyrimidinyl |
| 2,4-Difluorophenyl | 5-Chloro-6-methyl-4-pyrimidinyl |
|  | 3-Pyridazinyl |
|  | 6-Chloro-3-pyridazinyl |
|  | 2-Pyrazinyl |

TABLE 6

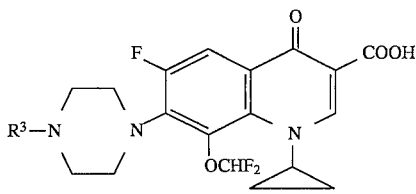

| R³ | R³ |
|---|---|
| Phenyl | 2-Oxazolyl |
| 2-Fluorophenyl | 2-Thiazolyl |
| 3-Fluorophenyl | 2-Imidazolyl |
| 4-Fluorophenyl | 2-Pyridyl |
| 2-Chlorophenyl | 6-Methoxy-2-pyridyl |
| 3-Chlorophenyl | 3-Nitro-2-pyridyl |
| 4-Chlorophenyl | 3-Amino-2-pyridyl |
| 2-Methoxyphenyl | 3-Methylamino-2-pyridyl |
| 3-Methoxyphenyl | 3-Ethylamino-2-pyridyl |
| 4-Methoxyphenyl | 3-Fluoro-2-pyridyl |
| 2-Nitrophenyl | 3-Pyridyl |
| 3-Nitrophenyl | 4-Pyridyl |
| 4-Nitrophenyl | 2-Benzoxazolyl |
| 2-Aminophenyl | 5-Chloro-2-benzoxazolyl |
| 3-Aminophenyl | 2-Benzothiazolyl |
| 4-Aminophenyl | 5-Methyl-2-benzothiazolyl |
| 2-Dimethylaminophenyl | 2-Benzimidazolyl |
| 3-Dimethylaminophenyl | 2-Pyrimidinyl |
| 4-Dimethylaminophenyl | 5-Chloro-2-pyrimidinyl |
| 2-Trifluoromethylphenyl | 4-Methoxy-2-pyrimidinyl |
| 3-Trifluoromethylphenyl | 4,6-Dimethoxy-2-pyrimidinyl |
| 4-Trifluoromethylphenyl | 4-Pyrimidinyl |
| 2,4-Difluorophenyl | 5-Chloro-6-methyl-4-pyrimidinyl |
| 4-Methylphenyl | 3-Pyridazinyl |
| 4-Hydroxyphenyl | 6-Chloro-3-pyridazinyl |
|  | 2-Pyrazinyl |

TABLE 7

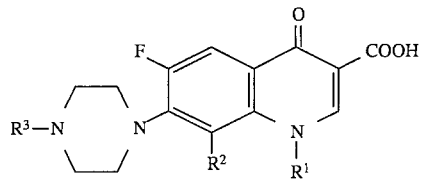

| R¹ | R² | R³ |
|---|---|---|
| Methyl | Methoxy | 3-Chlorophenyl |
| 4-Fluorophenyl | Methoxy | 4-Nitrophenyl |
| 2,4-Difluorophenyl | Methoxy | 4-Dimethylaminophenyl |
| Methyl | Difluoromethoxy | 2-Methylphenyl |
| Methyl | Difluoromethoxy | 2-Methoxyphenyl |
| Methyl | Difluoromethoxy | 3-Methoxyphenyl |
| Methyl | Difluoromethoxy | 4-Methoxyphenyl |
| Methyl | Difluoromethoxy | 2-Hydroxyphenyl |
| Methyl | Difluoromethoxy | 4-Chlorophenyl |
| Methyl | Difluoromethoxy | 4-Fluorophenyl |
| Methyl | Difluoromethoxy | 2-Pyridyl |
| Methyl | Difluoromethoxy | 2-Pyrimidinyl |
| Isopropyl | Difluoromethoxy | 2-Methoxyphenyl |
| Isopropyl | Difluoromethoxy | 2-Pyrimidinyl |
| 4-Fluorophenyl | Difluoromethoxy | 2-Aminophenyl |
| 2,4-Difluorophenyl | Difluoromethoxy | 2-Trifluoromethylphenyl |
| Cyclobutyl | Difluoromethoxy | 2-Pyrimidinyl |
| Cycloheptyl | Difluoromethoxy | 2-Pyrimidinyl |
| Cyclohexyl | Difluoromethoxy | 2-Pyrimidinyl |
| Methoxy | Difluoromethoxy | 2-Pyrimidinyl |
| 2-Fluorocyclopropyl | Difluoromethoxy | 2-Pyrimidinyl |
| Ethyl | Ethoxy | 2-Methoxyphenyl |
| H | Difluoromethoxy | 2-Methoxyphenyl |
| 2-Hydroxyethyl | Difluoromethoxy | 2-Methoxyphenyl |
| 2-Acetoxyethyl | Difluoromethoxy | 2-Methoxyphenyl |
| Carboxymethyl | Difluoromethoxy | 2-Methoxyphenyl |
| 2-Dimethylaminoethyl | Difluoromethoxy | 2-Methoxyphenyl |
| 2-Morpholinoethyl | Difluoromethoxy | 2-Methoxyphenyl |
| 2-Pyridylmethyl | Difluoromethoxy | 2-Methoxyphenyl |
| Methylamino | Difluoromethoxy | 2-Methoxyphenyl |
| 2-Hydroxyethyl | Difluoromethoxy | 2-Pyrimidinyl |
| Methylamino | Difluoromethoxy | 2-Pyrimidinyl |
| Vinyl | Difluoromethoxy | 2-Pyrimidinyl |
| 2-Propenyl | Difluoromethoxy | 2-Pyrimidinyl |
| Ethynyl | Difluoromethoxy | 2-Pyrimidinyl |
| 2-Propynyl | Difluoromethoxy | 2-Pyrimidinyl |
| Cyclopropylmethyl | Difluoromethoxy | 2-Pyrimidinyl |
| 2,4-Difluorophenyl | Difluoromethoxy | 2-Pyrimidinyl |

TABLE 8

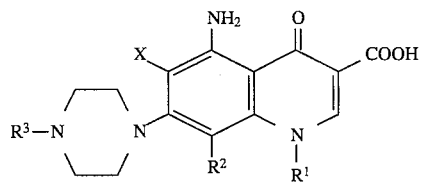

| X | R¹ | R² | R³ |
|---|---|---|---|
| F | Ethyl | Methoxy | 2,4-Dichlorophenyl |
| Cl | Ethyl | Methoxy | 3,4-Dichlorophenyl |
| Cl | Ethyl | Methoxy | 1-Naphthyl |
| Cl | Ethyl | Methoxy | 2-Naphthyl |
| F | 2-Fluoroethyl | Methoxy | 2,4-Dichlorophenyl |
| Cl | 2-Fluoroethyl | Methoxy | 3,4-Dichlorophenyl |
| Cl | 2-Fluoroethyl | Methoxy | 1-Naphthyl |
| Cl | 2-Fluoroethyl | Methoxy | 2-Naphthyl |
| F | Cyclopropyl | Methoxy | 2,4-Dichlorophenyl |
| Cl | Cyclopropyl | Methoxy | 3,4-Dichlorophenyl |
| Cl | Cyclopropyl | Ethoxy | 1-Naphthyl |

TABLE 8-continued

[Structure: quinolone with NH2, X, R3-N-piperazinyl, R2, R1, COOH]

| X | R¹ | R² | R³ |
|---|---|---|---|
| Cl | Cyclopropyl | Propoxy | 2-Naphthyl |
| F | Ethyl | Difluoromethoxy | 2,4-Difluorophenyl |
| Cl | Ethyl | Difluoromethoxy | 2,4-Dichlorophenyl |
| Cl | Ethyl | Difluoromethoxy | 3,4-Dichlorophenyl |
| Cl | Ethyl | Fluoromethoxy | 1-Naphthyl |
| Cl | Ethyl | Trifluoromethoxy | 2-Naphthyl |
| F | 2-Fluoroethyl | Difluoromethoxy | 2,4-Difluorophenyl |
| Cl | 2-Fluoroethyl | Difluoromethoxy | 2,4-Dichlorophenyl |
| Cl | 2-Fluoroethyl | Difluoromethoxy | 3,4-Dichlorophenyl |
| Cl | 2-Fluoroethyl | Fluoromethoxy | 1-Naphthyl |
| Cl | 2-Fluoroethyl | Trifluoromethoxy | 2-Naphthyl |
| F | Cyclopropyl | Difluoromethoxy | 2,4-Dichlorophenyl |
| Cl | Cyclopropyl | Difluoromethoxy | 3,4-Dichlorophenyl |
| Cl | Cyclopropyl | Fluoromethoxy | 1-Naphthyl |
| Cl | Cyclopropyl | Trifluoromethoxy | 2-Naphthyl |
| F | Cyclopropyl | Fluoromethoxy | 2-Oxazolyl |
| F | Cyclopropyl | Difluoromethoxy | 2-Pyridyl |
| F | Isopropyl | Difluoromethoxy | 2-Methoxyphenyl |

TABLE 9

[Structure: quinolone with F, R4, R5, R3-N, (CH2)n, R2, R1, COOH]

| R¹ | R² | n | R³ | R⁴ | R⁵ |
|---|---|---|---|---|---|
| Ethyl | Methoxy | 2 | 2-Pyridyl | H | H |
| 2-Fluoroethyl | Methoxy | 2 | 2-Pyridyl | H | H |
| Cyclopropyl | Methoxy | 2 | 2-Pyridyl | H | H |
| Ethyl | Methoxy | 2 | 2-Pyrimidinyl | H | H |
| 2-Fluoroethyl | Methoxy | 2 | 2-Pyrimidinyl | H | H |
| Cyclopropyl | Methoxy | 2 | 2-Pyrimidinyl | H | H |
| Ethyl | Methoxy | 1 | 2-Pyrimidinyl | Methyl | H |
| 2-Fluoroethyl | Methoxy | 1 | 2-Pyrimidinyl | Methyl | H |
| Cyclopropyl | Methoxy | 1 | 2-Pyrimidinyl | Methyl | H |
| Ethyl | Methoxy | 1 | 2-Pyridyl | Methyl | H |
| 2-Fluoroethyl | Methoxy | 1 | 2-Pyridyl | Methyl | H |
| Cyclopropyl | Methoxy | 1 | 2-Pyridyl | Methyl | H |
| Ethyl | Difluoromethoxy | 2 | 2-Pyridyl | H | H |
| 2-Fluoroethyl | Difluoromethoxy | 2 | 2-Pyridyl | H | H |
| Cyclopropyl | Difluoromethoxy | 2 | 2-Pyridyl | H | H |
| Ethyl | Difluoromethoxy | 2 | 2-Pyrimidinyl | H | H |
| 2-Fluoroethyl | Difluoromethoxy | 2 | 2-Pyrimidinyl | H | H |
| Cyclopropyl | Difluoromethoxy | 2 | 2-Pyrimidinyl | H | H |
| Ethyl | Difluoromethoxy | 1 | 2-Pyrimidinyl | Methyl | H |
| 2-Fluoroethyl | Difluoromethoxy | 1 | 2-Pyrimidinyl | Methyl | H |
| Cyclopropyl | Difluoromethoxy | 1 | 2-Pyrimidinyl | Methyl | H |

TABLE 9-continued

| R¹ | R² | n | R³ | R⁴ | R⁵ |
|---|---|---|---|---|---|
| Ethyl | Difluoromethoxy | 1 | 2-Pyridyl | Methyl | H |
| 2-Fluoroethyl | Difluoromethoxy | 1 | 2-Pyridyl | Methyl | H |
| Cyclopropyl | Difluoromethoxy | 1 | 2-Pyridyl | Methyl | H |
| Methyl | Difluoromethoxy | 1 | 2-Pyrimidinyl | Methyl | Methyl |
| Ethyl | Difluoromethoxy | 1 | 2-Pyrimidinyl | Methyl | Methyl |
| Cyclopropyl | Difluoromethoxy | 1 | 2-Pyrimidinyl | Methyl | Methyl |

TABLE 10

[Structure: quinolone with F, R3-N-piperazinyl, R2, R1, COOH]

| R¹ | R² | R³ |
|---|---|---|
| Cyclopropyl | H | 2-Methoxyphenyl |
| Ethyl | H | 2-Methoxyphenyl |
| 2-Fluorophenyl | H | 3-Methoxyphenyl |
| 4-Fluorophenyl | H | 4-Trifluoromethylphenyl |
| 2,4-Difluorophenyl | H | 3-Aminophenyl |
| Cyclopropyl | H | 2-Pyridyl |
| Ethyl | H | 2-Pyridyl |
| 2-Fluoroethyl | H | 2-Pyridyl |
| 4-Fluorophenyl | H | 2-Pyridyl |
| Cyclopropyl | F | 2-Methoxyphenyl |
| Methyl | F | 2-Fluorophenyl |
| Ethyl | F | 2-Methoxyphenyl |
| 2-Fluoroethyl | F | 2-Methoxyphenyl |
| 2-Fluoroethyl | F | 2-Pyridyl |
| Cyclopropyl | F | 2-Pyridyl |
| 4-Fluorophenyl | F | 4-Methoxyphenyl |
| 2,4-Difluorophenyl | F | 4-Aminophenyl |
| Methyl | Cl | 3-Fluorophenyl |
| 4-Fluorophenyl | Cl | 2-Nitrophenyl |
| 2,4-Difluorophenyl | Cl | 2-Dimethylaminophenyl |
| Methyl | Br | 4-Fluorophenyl |
| Methyl | Methyl | 2-Chlorophenyl |
| 4-Fluorophenyl | Methyl | 3-Nitrophenyl |
| 2,4-Difluorophenyl | Methyl | 3-Dimethylaminophenyl |
| Ethyl | Trifluoromethyl | 2-Pyrimidinyl |
| Cyclopropyl | H | 2-Pyrimidinyl |
| t-Butyl | H | 2-Pyrimidinyl |
| 2,4-Difluorophenyl | H | 2-Pyrimidinyl |
| 2-Fluoroethyl | F | 2-Pyrimidinyl |
| 2-Hydroxyethyl | F | 2-Pyrimidinyl |
| Ethyl | Cl | 2-Pyrimidinyl |
| Ethyl | Methyl | 2-Pyrimidinyl |

TABLE 11

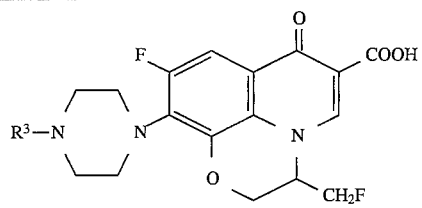

| R³ | R³ |
|---|---|
| Phenyl | 2-Oxazolyl |
| 2-Fluorophenyl | 2-Thiazolyl |
| 3-Fluorophenyl | 2-Imidazolyl |
| 4-Fluorophenyl | 2-Pyridyl |
| 2-Chlorophenyl | 6-Methoxy-2-pyridyl |
| 3-Chlorophenyl | 3-Nitro-2-pyridyl |
| 4-Chlorophenyl | 4-Amino-2-pyridyl |
| 2-Methoxyphenyl | 3-Methylamino-2-pyridyl |
| 3-Methoxyphenyl | 3-Ethylamino-2-pyridyl |
| 4-Methoxyphenyl | 3-Fluoro-2-pyridyl |
| 2-Nitrophenyl | 3-Pyridyl |
| 3-Nitrophenyl | 4-Pyridyl |
| 4-Nitrophenyl | 2-Benzoxazolyl |
| 2-Aminophenyl | 5-Chloro-2-benzoxazolyl |
| 3-Aminophenyl | 2-Benzothiazolyl |
| 4-Aminophenyl | 5-Methyl-2-benzothiazolyl |
| 2-Dimethylaminophenyl | 2-Benzimidazolyl |
| 3-Dimethylaminophenyl | 2-Pyrimidinyl |
| 4-Dimethylaminophenyl | 5-Chloro-2-pyrimidinyl |
| 2-Trifluoromethylphenyl | 4-Methoxy-2-pyrimidinyl |
| 3-Trifluoromethylphenyl | 4,6-Dimethoxy-2-pyrimidinyl |
| 4-Trifluoromethylphenyl | 4-Pyrimidinyl |
| 2,4-Difluorophenyl | 5-Chloro-6-methyl-4-pyrimidinyl |
| | 3-Pyridazinyl |
| | 6-Chloro-3-pyridazinyl |
| | 2-Pyrazinyl |

TABLE 12

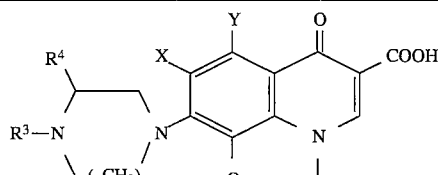

| X | Y | n | R³ | R⁴ |
|---|---|---|---|---|
| Cl | H | 1 | 2,4-Dichlorophenyl | H |
| Cl | H | 1 | 3,4-Dichlorophenyl | H |
| Cl | Amino | 1 | 1-Naphthyl | H |
| Cl | Amino | 1 | 2-Naphthyl | H |
| F | H | 2 | 2-Pyridyl | H |
| F | H | 2 | 2-Pyrimidinyl | H |
| F | H | 1 | 2-Pyridyl | Methyl |
| F | H | 1 | 2-Pyrimidinyl | Methyl |

TABLE 13

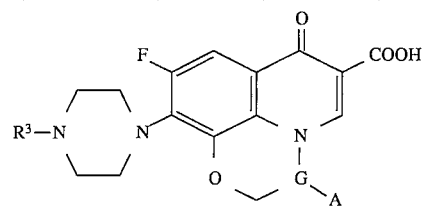

| R³ | G | A | R³ | G | A |
|---|---|---|---|---|---|
| 2-Fluorophenyl | CH | CH₃ | 2-Oxazolyl | CH | CH₃ |
| 3-Fluorophenyl | CH | CH₃ | 2-Thiazolyl | CH | CH₃ |
| 4-Fluorophenyl | CH | CH₃ | 2-Imidazolyl | CH | CH₃ |
| 2-Chlorophenyl | CH | CH₃ | 2-Pyridyl | CH | CH₃ |
| 3-Chlorophenyl | CH | CH₃ | 6-Methoxy-2-pyridyl | CH | CH₃ |
| 4-Chlorophenyl | CH | CH₃ | 3-Nitro-2-pyridyl | CH | CH₃ |
| 2-Methoxyphenyl | CH | CH₃ | 3-Amino-2-pyridyl | CH | CH₃ |
| 3-Methoxyphenyl | CH | CH₃ | 3-Methylamino-2-pyridyl | CH | CH₃ |
| 4-Methoxyphenyl | CH | CH₃ | 3-Ethylamino-2-pyridyl | CH | CH₃ |
| 2-Nitrophenyl | CH | CH₃ | 3-Fluoro-2-pyridyl | CH | CH₃ |
| 3-Nitrophenyl | CH | CH₃ | 3-Pyridyl | CH | CH₃ |
| 4-Nitrophenyl | CH | CH₃ | 4-Pyridyl | CH | CH₃ |
| 2-Aminophenyl | CH | CH₃ | 2-Benzoxazolyl | CH | CH₃ |
| 3-Aminophenyl | CH | CH₃ | 5-Chloro-2-benzoxazolyl | CH | CH₃ |
| 4-Aminophenyl | CH | CH₃ | 2-Benzothiazolyl | CH | CH₃ |
| 2-Dimethylaminophenyl | CH | CH₃ | 5-Methyl-2-benzothiazolyl | CH | CH₃ |
| 3-Dimethylaminophenyl | CH | CH₃ | 2-Benzimidazolyl | CH | CH₃ |
| 4-Dimethylaminophenyl | CH | CH₃ | 2-Pyrimidinyl | CH | CH₃ |
| 2-Trifluoromethylphenyl | CH | CH₃ | 5-Chloro-2-pyrimidinyl | CH | CH₃ |
| 3-Trifluoromethylphenyl | CH | CH₃ | 4-Methoxy-2-pyrimidinyl | CH | CH₃ |
| 4-Trifluoromethylphenyl | CH | CH₃ | 4,6-Dimethoxy-2-pyrimidinyl | CH | CH₃ |
| 2,4-Difluorophenyl | CH | CH₃ | 4-Pyrimidinyl | CH | CH₃ |
| 2-Pyrimidinyl | CH | CH₂Cl | 5-Chloro-6-methyl-4-pyrimidinyl | CH | CH₃ |
| 2-Pyrimidinyl | CH | CH₂OH | 3-Pyridazinyl | CH | CH₃ |
| 2-Pyrimidinyl | CH | CH₂OCH₃ | 6-Chloro-3-pyridazinyl | CH | CH₃ |
| | | | 2-Pyrazinyl | CH | CH₃ |
| | | | 2-Pyrimidinyl | CH | H |
| | | | 2-Pyrimidinyl | N | CH₃ |

TABLE 14

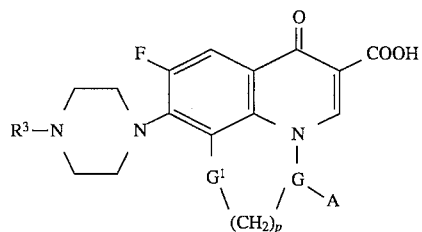

| R³ | G | G¹ | A | p |
|---|---|---|---|---|
| 2-Pyrimidinyl | CH | S | H | 1 |
| 2-Pyrimidinyl | CH | S | CH₃ | 1 |

TABLE 14-continued

| R³ | G | G¹ | A | p |
|---|---|---|---|---|
| 2-Pyrimidinyl | CH | S | CH₂F | 1 |
| 2-Pyrimidinyl | CH | NH | CH₃ | 1 |
| 2-Pyrimidinyl | CH | NCH₃ | CH₃ | 1 |
| 2-Pyrimidinyl | CH | CH₂ | H | 1 |
| 2-Pyrimidinyl | CH | CH₂ | CH₃ | 1 |
| 2-Pyrimidinyl | CH | CH₂ | CH₂F | 1 |
| 2-Pyrimidinyl | CH | CH₂ | H | 0 |
| 2-Pyrimidinyl | CH | CH₂ | CH₃ | 0 |
| 2-Pyrimidinyl | N | CH₂ | CH₃ | 1 |
| 2-Pyrimidinyl | CH | CO | CH₃ | 1 |

TABLE 15

| X | Y | n | R³ | R⁴ |
|---|---|---|---|---|
| Cl | H | 1 | 2,4-Dichlorophenyl | H |
| Cl | H | 1 | 3,4-Dichlorophenyl | H |
| Cl | Amino | 1 | 1-Naphthyl | H |
| Cl | Amino | 1 | 2-Naphthyl | H |
| F | H | 2 | 2-Pyridyl | H |
| F | H | 2 | 2-Pyrimidinyl | H |
| F | H | 1 | 2-Pyridyl | Methyl |
| F | H | 1 | 2-Pyrimidinyl | Methyl |

TABLE 16

| R¹ | R³ |
|---|---|
| Cyclopropyl | 2-Pyridyl |
| Ethyl | 2-Pyridyl |
| 2-Fluoroethyl | 2-Pyridyl |
| 4-Fluorophenyl | 2-Methoxyphenyl |
| Ethyl | 2-Methoxyphenyl |
| Ethyl | 2-Pyrimidinyl |

TABLE 16-continued

| R¹ | R³ |
|---|---|
| 2,4-Difluorophenyl | 2-Pyrimidinyl |

TABLE 17

| X | Y | Z | R¹ | R² | R³ |
|---|---|---|---|---|---|
| H | H | Carboxyl | Ethyl | Difluoromethoxy | 2-Pyrimidinyl |
| F | H | 5-Tetrazolyl | Ethyl | Difluoromethoxy | 2-Pyrimidinyl |
| F | F | Carboxyl | Cyclopropyl | F | 2-pyrimidinyl |
| F | H | Ethoxycarbonyl | Ethyl | Difluoromethoxy | 2-Pyrimidinyl |
| F | H | 2-Morpholinoethoxycarbonyl | Ethyl | Difluoromethoxy | 2-Pyrimidinyl |
| F | H | 2-Piperidinoethoxycarbonyl | Ethyl | Difluoromethoxy | 2-Pyrimidinyl |
| F | H | 2-(4-methylpiperidino)-ethoxycarbonyl | Ethyl | Difluoromethoxy | 2-Pyrimidinyl |
| F | H | 2-Morpholinoethoxycarbonyl | Methyl | Difluoromethoxy | 2-Methoxyphenyl |
| F | Methyl | Carboxyl | Ethyl | H | 2-Methoxyphenyl |
| F | Methylamino | Carboxyl | Ethyl | Difluoromethoxy | 2-Pyrimidinyl |
| F | Dimethylamino | Carboxyl | Ethyl | Difluoromethoxy | 2-Pyrimidinyl |
| F | Benzylamino | Carboxyl | Ethyl | Difluoromethoxy | 2-Pyrimidinyl |
| F | Benzylamino | Carboxyl | Ethyl | Difluoromethoxy | Phenyl |
| F | H | Acetoxymethoxycarbonyl | Ethyl | Difluoromethoxy | 2-Pyrimidinyl |

TABLE 18

| R⁶ | R⁷ | R⁸ | m | n' | n" |
|---|---|---|---|---|---|
| 2-Pyrimidinyl | H | H | 0 | 1 | 2 |
| Phenyl | H | 4-OH | 0 | 1 | 2 |
| Phenyl | H | 4-OCH3 | 0 | 1 | 2 |
| 2-Pyrimidinyl | Methyl | H | 0 | 1 | 2 |
| 2-Pyrimidinyl | H | H | 1 | 1 | 2 |
| 2-Pyrimidinyl | Methyl | H | 1 | 1 | 2 |
| 2-Pyrimidinyl | H | H | 0 | 2 | 2 |
| 2-Pyrimidinyl | Methyl | H | 0 | 2 | 2 |
| 2-Pyrimidinyl | H | H | 0 | 1 | 3 |
| 2-Pyrimidinyl | H | H | 0 | 1 | 1 |

TABLE 19

| R² | R³ | T |
|---|---|---|
| H | 2-Pyrimidinyl | CH(CH₃)₂ |
| Methoxy | 2-Pyrimidinyl | CH(CH₃)₂ |
| Difluoromethoxy | 2-Pyrimidinyl | CH(CH₃)₂ |
| Difluoromethoxy | 2-Pyrimidinyl | cyclopropyl |
| Difluoromethoxy | 2-Pyrimidinyl | cyclopropenyl |
| Difluoromethoxy | 2-Pyrimidinyl | methylcyclopropenyl |

TABLE 20

| R¹ | R² | R³ | W |
|---|---|---|---|
| Ethyl | Difluoromethoxy | 2-Pyrimidinyl | S |
| Ethyl | Methoxy | 2-Pyrimidinyl | S |
| Ethyl | Difluoromethoxy | 2-Pyrimidinyl | O |
| Ethyl | Methoxy | 2-Pyrimidinyl | O |
| Ethyl | Difluoromethoxy | 2-Pyridyl | S |
| Ethyl | Methoxy | 2-Pyridyl | S |

Among the above compounds of the present invention, the following compounds are preferred:

1-cyclopropyl-6-fluoro-8-difluoromethoxy-7-[4-(2-methoxyphenyl)piperazin-1-yl]-1,4 -dihydro-4-oxoquinoline-3-carboxylic acid, 1-cyclopropyl-6-fluoro-8-difluoromethoxy-7-(4-phenylpiperazin-1-yl)-1,4-dihydro-4 -oxoquinoline-3-carboxylic acid, 1-cyclopropyl-6-fluoro-8-difluoromethoxy-7-[4-(4-methoxyphenyl)piperazin-1-yl]-1,4 -dihydro-4-oxoquinoline-3carboxylic acid, 1-cyclopropyl-6-fluoro-8-difluoromethoxy-7-[4-(2-pyrimidinyl)piperazin-1-yl]-1,4 -dihydro-4-oxoquinoline-3-carboxylic acid, 6-fluoro-8-difluoromethoxy-1-methyl-7-[4-(2-methoxyphenyl)piperazin-1-yl]-1,4 -dihydro-4-oxoquinoline-3-carboxylic acid, 6-fluoro-8-difluoromethoxy-1-methyl-7-[4-(2-pyrimidinyl)piperazin-1-yl]-1,4 -dihydro-4-oxoquinoline-3-carboxylic acid, 1-(2-acetoxyethyl)-6-fluoro-8-difluoromethoxy-7-[4-(2-methoxyphenyl)piperazin-1-yl] -1,4-dihydro-4-oxoquinoline-3-carboxylic acid, 1-ethyl-6-fluoro-8-difluoromethoxy-7-[4-(2-methoxyphenyl)piperazin-1-yl]-1,4 -dihydro-4-oxoquinoline-3-carboxylic acid, 1-ethyl-6-fluoro-8-difluoromethoxy-7-[4-(2-pyrimidinyl)piperazin-1-yl]-1,4 -dihydro-4-oxoquinoline-3-carboxylic acid, 9-fluoro-3-fluoromethyl-10-[4-(2-pyrimidinyl)piperazin-1yl]-2,3-dihydro-7-oxo-7H -pyrido[1,2,3-de][1,4 ]benzoxazine-6-carboxylic acid, 2-morpholinoethyl 1-ethyl-6-fluoro-8-difluoromethoxy-7-[4-(2-pyrimidinyl)piperazin-1 -yl]-1,4-dihydro-4-oxoquinoline-3-carboxylate, ethyl 1-ethyl-6-fluoro-8-difluoromethoxy-7-[4-(2-pyrimidinyl)piperazin-1-yl]-1,4 -dihydro-4 -oxoquinoline-3-carboxylate, 2-piperidinoethyl 1-ethyl-6-fluoro-8-difluoromethoxy-7-[4-(2-pyrimidinyl) piperazin-1-yl ]-1,4-dihydro-4-oxoquinoline-3-carboxylate, 2-(4-methylpiperidino) ethyl 1-ethyl-6-fluoro-8-difluoromethoxy-7- [4- (2-pyrimidinyl) piperazin-1-yl]-1,4-dihydro-4-oxoquinoline-3-carboxylate and 2-morpholinoethyl 6-fluoro-8-difluoromethoxy-1-methyl-7-[4-(2-methoxyphenyl)piperazin-1-yl ]-1,4-dihydro-4-oxoquinoline-3-carboxylate, and 1-ethyl-6-fluoro-8-difluoromethoxy-7-[4-(2-pyrimidinyl )piperazin-1-yl]-1,4-dihydro -4-oxoquinoline-3-carboxylic acid is particularly preferred.

The compounds represented by the above formulae (Ia), (Ib) and (Ic) can be prepared by Method A shown below.

In the case of the compound represented by the formula (Ia), it can be also prepared by Method B shown below.

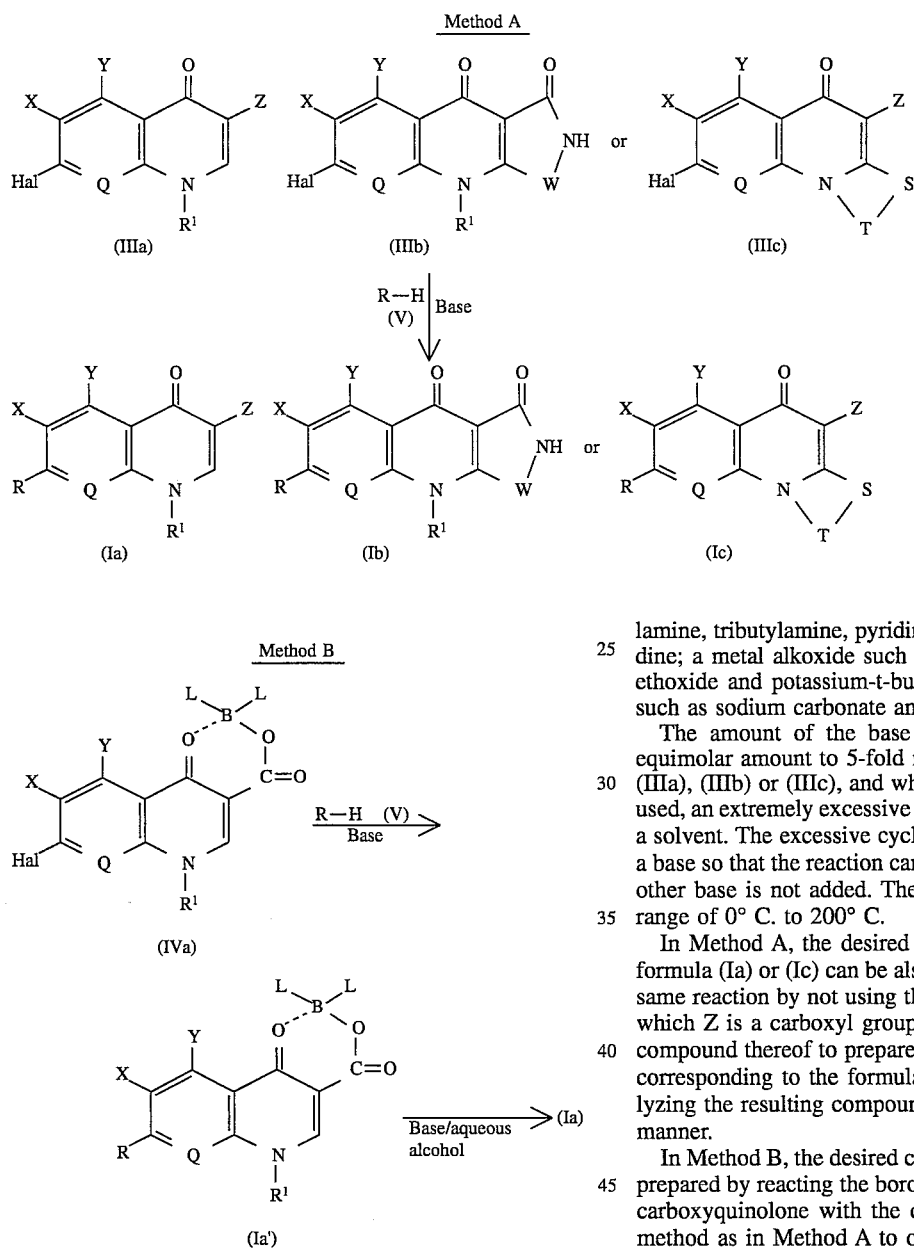

Method A

Method B wherein R, R¹, Q, T W X, Y and Z each have the same meanings as defined above; Hal represents a halogen atom; and L represents a fluorine atom or an acetoxy group.

In Method A, the desired compound of the formula (Ia), (Ib) or (Ic) is prepared by coupling the quinolone derivative (IIIa), (IIIb) or (IIIc) with the cyclic amine derivative (V) in the presence or absence of a base and in the presence or absence of a solvent.

As the solvent to be used in this reaction, there may be preferably used an aprotic polar solvent such as dimethyl sulfoxide, N,N-dimethylformamide, hexamethylphosphoric triamide and N,N-dimethylacetamide, and in addition, there may be also used ketones such as acetone and methyl ethyl ketone; ethers such as diethyl ether, tetrahydrofuran and dioxane; esters such as ethyl acetate; alcohols such as methanol, ethanol, propanol, isopropanol and butanol; and nitriles such as acetonitrile. As the base, there may be exemplified tertiary amines such as 1,8-diazabicyclo[5.4.0]-7-undecene, 1,5-diazabicyclo[4.3.0]-5-nonene, triethylamine, tributylamine, pyridine, picoline, lutidine and collidine; a metal alkoxide such as sodium methoxide, sodium ethoxide and potassium-t-butoxide; and an inorganic base such as sodium carbonate and potassium carbonate.

The amount of the base to be used is preferably an equimolar amount to 5-fold moles based on the compound (IIIa), (IIIb) or (IIIc), and when the above tertiary amine is used, an extremely excessive amount thereof may be used as a solvent. The excessive cyclic amine (V) also functions as a base so that the reaction can proceed smoothly even when other base is not added. The reaction is carried out in the range of 0° C. to 200° C.

In Method A, the desired compound represented by the formula (Ia) or (Ic) can be also obtained by carrying out the same reaction by not using the compound (IIIa) or (IIIc) in which Z is a carboxyl group but using a lower alkyl ester compound thereof to prepare a lower alkyl ester compound corresponding to the formula (Ia) or (Ic), and then hydrolyzing the resulting compound according to a conventional manner.

In Method B, the desired compound of the formula (Ia) is prepared by reacting the boron chelate compound (IVa) of a carboxyquinolone with the cyclic amine (V) by the same method as in Method A to obtain the compound (Ia'), and then reacting the compound (Ia') in an aqueous alcohol in the presence of a base whereby decomposing the chelate.

As the base to be used for decomposing the chelate in the above Method B, there may be mentioned an alkali hydroxide such as sodium hydroxide and potassium hydroxide; an alkali carbonate such as sodium carbonate and potassium carbonate; tertiary amines such as 1,8-diazabicyclo[5.4.0]-7-undecene, 1,5-diazabicyclo[4.3.0]-5-nonene, triethylamine and 4-dimethylaminopyridine; or a metal alkoxide such as sodium methoxide, sodium ethoxide and potassium-t-butoxide.

In the reaction described above, after completion of the reaction, the desired compound can be obtained by treating the reaction mixture according to a conventional manner, and, if necessary, it can be purified by a conventional purification means such as recrystallization and column chromatography.

The compounds of the formulae (Ia), (Ib) and (Ic) thus obtained are made into desired salts according to a conventional manner, if necessary.

The compounds of the above formulae (Ia), (Ib) and (Ic) wherein $R^3$ in the substituent R is an aromatic heterocyclic group can be also prepared by Method C shown below.

Method C

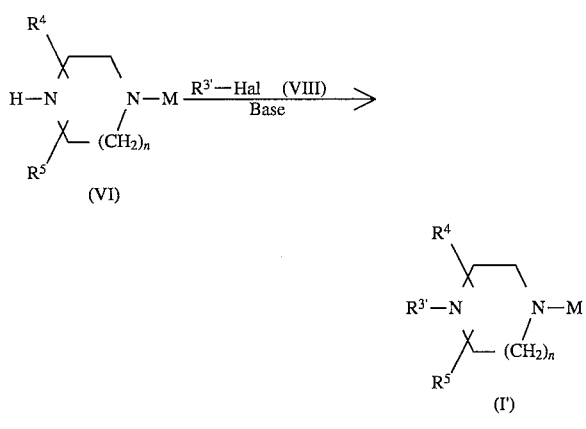

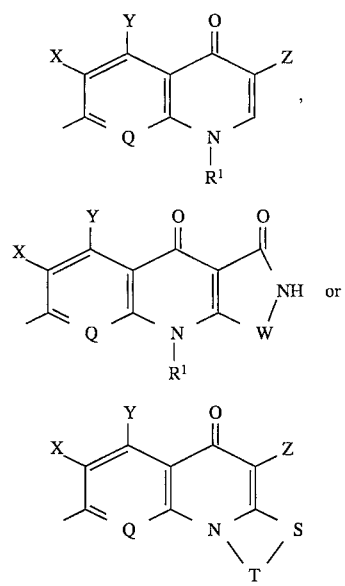

wherein $R^4$, $R^5$, $R^7$, $R^8$, m, n, n', n" and Hal each have the same meanings as defined above; $R^{3'}$ and $R^{6'}$ represent the aromatic heterocyclic groups mentioned in the description of $R^3$ and $R^{6'}$ and M represents a formula of (Ma), (Mb) or (Mc),

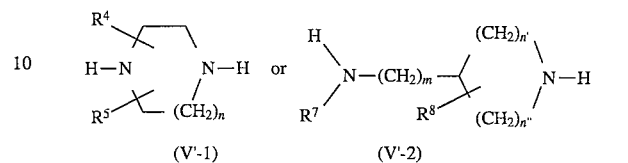

wherein $R^1$, Q, T, W, X, Y and Z each have the same meanings as defined above.

The reaction of Method C is carried out in the same manner as in Method A.

The compounds (VI) and (VII) which are used as starting materials in Method C can be prepared by using the compound (IIIa), (IIIb), (IIIc) or (IVa) as a starting compound and reacting said starting compound in the same manner as in Method A or Method B by using the cyclic amine (V'-i) or (V'-2) shown below in place of the above cyclic amine (V).

wherein $R^4$, $R^5$, $R^7$, $R^8$, m, n, n' and n" each have the same meanings as defined above.

The compound of the above formula (Ia) or (Ic) wherein Z is a 5-tetrazolyl group can be also prepared from a corresponding cyano compound of the formula (IX) or (X), respectively, by Method D shown below.

Method D

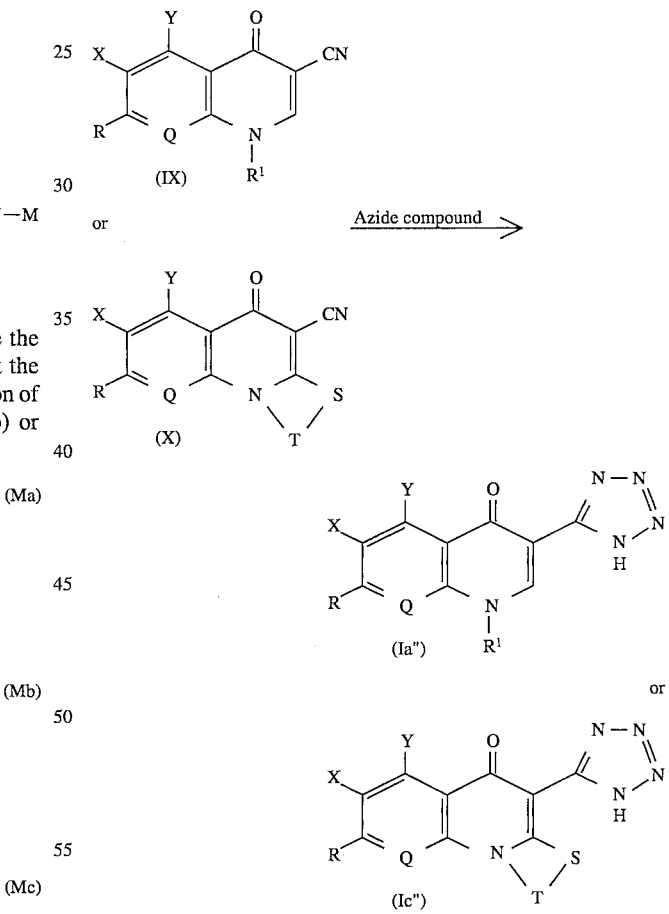

wherein R, $R^1$, Q, T, X and Y each have the same meanings as defined above.

In Method D, the compound (Ia") or (Ic") is synthesized by reacting the compound (IX) or (X) with a 1- to 10-fold molar amount, preferably a 1- to 5-fold molar amount of an azide compound in a solvent.

As the azide compound to be used in the reaction, there may be mentioned, for example, alkali metal azides such as sodium azide, potassium azide and lithium azide; alkaline earth metal azides such as calcium azide and magnesium azide; and organic tin azides such as tributyltin azide and triphenyltin azide. In said reaction, the azide compound may be used singly or may be used in combination with, for example, a Lewis acid such as aluminum chloride, stannic chloride, zinc chloride, titanium chloride, tri(butyl)tin chloride and a trifluoroboran-diethyl ether complex; ammonium salts such as ammonium chloride and tetramethylammonium chloride; sulfonic acids such as methanesulfonic acid and ethanesulfonic acid; alkali metal chlorides such as lithium chloride; and amine salts such as triethylamine hydrochloride. As a use example of the above azide compound, there may be also employed a method in which tri(butyl)tin azide is formed from tri(butyl)tin chloride and sodium azide in a system, and then provided for use.

The solvent to be used is not particularly limited so long as it is inactive to the reaction, and may include, for example, aprotic polar solvents such as N,N-dimethylformamide, dimethyl sulfoxide, N-methylpyrrolidone and N,N-dimethylacetamide; ethers such as tetrahydrofuran, dimethoxyethane, diethoxyethane and dioxane; aromatic hydrocarbons such as benzene, toluene and xylene; and aliphatic hydrocarbons such as hexane and petroleum ether.

The reaction temperature is in the range of 0° to 200° C., preferably 0° to 150° C. The reaction time varies depending on the other conditions, but it is generally 1 to 72 hours, preferably 3 to 48 hours.

In the above Method A and Method B, the compounds of the formulae (IIIb) and (IVa), and the compounds of the formulae (IIIa) and (IIIc) in which Z is a carboxyl group or lower alkyl ester compounds thereof which are used as starting materials, can be easily prepared by using corresponding starting materials suitably according to a known method, for example, methods described in Japanese Provisional Patent Publications No. 30964/1981, No. 74667/1983 (which corresponds to U.S. Pat. Nos. 4,620,007, 4,670,444 and No. 5,077,429, hereinafter the same), No. 90511/1983, No. 103393/1983 (U.S. Pat. No. 4,426,381), No. 67290/1984, No. 76091/1984, No. 56959/1985 (U.S. Pat. No. 4,730,000), No. 126271/1985, No. 163866/1985 (U.S. Pat. No. 4,774,246), No. 172981/1985, No. 174786/1985 (U.S. Pat. No. 4,616,019), No. 452/1987 (U.S. Pat. Nos. 4,762,831, No. 4,859,773 and No. 4,958,045), No. 53987/1987 (U.S. Pat. No. 4,720,495), No. 155282/1987, No. 187472/1987 (U.S. Pat. No. 4,767,762), No. 228063/1987, No. 132891/1988 (U.S. Pat. No. 4,801,584), No. 198664/1988 (U.S. Pat. No. 4,997,943), No. 264461/1988 (U.S. Pat. Nos. 4,855,292 and No. 4,935,420), No. 297366/1988, No. 124873/1990 (U.S. Pat. No. 5,073,556), No. 191257/1990 (U.S. Pat. No. 4,971,970), No. 231476/1990 (U.S. Pat. No. 5,073,556) and No. 209367/1991.

Among the compound of the formula (IIIa) or (IIIc), the compound of the formula (IIIa') or (IIIc') wherein Z is a 5-tetrazolyl group can be prepared from a corresponding cyano compound by Method E shown below.

Method E

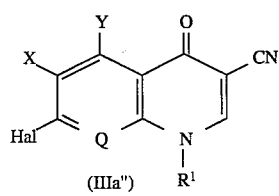
(IIIa")

-continued
Method E

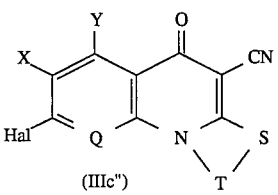
(IIIc")

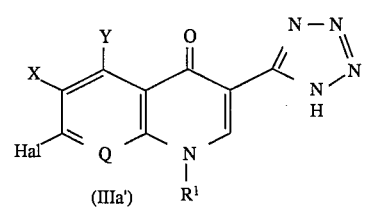
(IIIa')

or

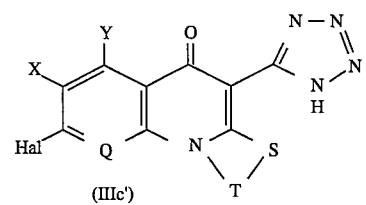
(IIIc')

wherein $R^1$, Q, T, X, Y and Hal each have the same meanings as defined above.

Method E is carried out in the same manner as in Method D. In Method E, the compounds of the formulae (IIIa") and (IIIc") which are used as starting compounds can be prepared by using various starting materials in which a part corresponding to a carboxyl group is a cyano group according to the methods described in the publications enumerated about the compounds of the above formulae (IIIa) and (IIIc) wherein Z is a carboxyl group.

In the compounds represented by the above formulae (Ia), (Ib) and (Ic) prepared as described above, optical isomers or geometrical (cis or trans) isomers may exist. In that case, optical isomers or geometrical isomers of the corresponding desired compounds of the formulae (Ia), (Ib) and (Ic) can be obtained by carrying out the above reaction using optically divided or separated starting compounds, if desired. Also, the respective stereoisomers can be also obtained by processing a mixture of optical isomers or geometrical isomers of the compounds represented by the formulae (Ia), (Ib) and (Ic) according to a conventional optical division method or separation method.

When the compounds represented by the above formulae (Ia), (Ib) and (Ic) have carboxyl groups in their molecules, the carboxyl groups may be protected to form esters as described above, and the ester formation reaction is carried out by using a corresponding carboxyl compound and a corresponding alcohol according to a conventional method (e.g. a dehydration condensation method by an acid catalyst, a method through an acid halide or a dehydration condensation method using a carbodiimide).

The compounds represented by the formulae (Ia), (Ib) and (Ic) are useful as an AIDS curing agent. The compounds of the present invention may be administered by any suitable route commonly used for antiviral compounds, and may be formulated in admixture with conventional additives or adjuvants for this purpose. For example, for oral administration, there may be formulated as tablets, capsules, granules, powders or syrup; whilst for parenteral administration, they may be formulated as injections or suppositories.

Where the compounds of the present invention are to be administered by injection, they may be administered by a conventional route such as, for example, by the intravascular, intraperitoneal, intramuscular or subcutaneous routes.

Injectable formulations will generally comprise a pharmaceutically acceptable carrier and, optionally, one or more additional antiviral compounds and, if necessary, substances to render the injection isotonic with the body fluids, as well as other ingredients as may be required, such as emulsifiers.

Injections may be sub-divided for separate administration, whether simultaneously or over a period of time, suitably weeks.

The pharmaceutical preparations of the present invention can be prepared by any conventional means, using such additives as vehicles, binders, disintegrators, lubricants, stabilizers and corrigents.

Although the dosage may vary, depending on the age, body weight and symptoms of the patient, for an adult human patient, a suitable daily dosage may be from about 100 to about 2000 mg, or from about 1 to about 25 mg/kg body weight, per day, which may be administered as a single dose or divided into several doses. When several-fold doses (calculated based on weight) of the above dose of the compounds of the formulae (Ia), (Ib) and (Ic) were orally administered to rats, toxicities thereof were not recognized.

EXAMPLES

The present invention will now be illustrated in more detail with reference to the accompanying Examples and Reference examples.

Example 1

Synthesis of 1-cyclopropyl-6-fluoro-8-difluoromethoxy-7-[4-(2-methoxyphenyl)piperazin-1-yl]-1,4-dihydro-4-oxo-quinoline-3-carboxylic acid.hydrochloride

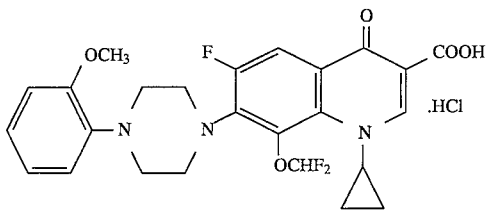

In 20 ml of pyridine were dissolved 1.66 g (0.005 mole) of 1-cyclopropyl-6,7-difluoro-8-difluoromethoxy-1,4-dihydro-4-oxoquinoline-3-carboxylic acid and 2.4 g (0.0125 mole) of 1-(2-methoxyphenyl)piperazine, and the mixture was stirred at 105° to 110° C. for 3 hours. Then, the solvent was removed under reduced pressure, and the residue was subjected to silica gel column chromatography (the eluent used was a mixture of chloroform:methanol =9.5:0.5) to obtain 1.33 g of of free title compound. Next, 1.33 g of the free compound was dissolved in 100 ml of a mixture of chloroform and methanol (4:1), and 2 ml of conc. hydrochloric acid was added thereto. The mixture was concentrated under reduced pressure, and the residue was washed with a mixture of methanol and ethanol (4:1), and dried to obtain 1.08 g of the title compound as white powder.

Melting point: 223° to 225° C.

NMR(DMSO-$d_6$, δ): 1.04 ~ 1.07 (2H, m), 1.16 ~ 1.17 (2H, m), 3.30 (4H, br.s), 3.47 (4H, br.s), 3.86 (3H, s), 4.09 ~ 4.12 (1H, m), 6.90 ~ 7.27 (5H, m), 7.95 ~ 7.98 (1H, d, J=12.1Hz), 8.79 (1H, s)

MS spectrum (CI): m/e 504 ($M^+$+1)

Examples 2 to 62

Using a similar method to Example 1, but using appropriate starting materials, the compounds shown in Table 21 were synthesized.

TABLE 21

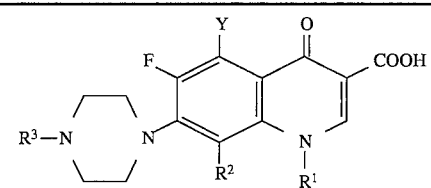

| Example | Y | $R^1$ | $R^2$ | $R^3$ | m.p. (°C.) |
|---|---|---|---|---|---|
| 2 | H | Cyclopropyl | Difluoromethoxy | Phenyl | 209 to 211 |
| 3 | H | Cyclopropyl | Difluoromethoxy | 2-Chlorophenyl | 281 to 284 |
| 4 | H | Cyclopropyl | Difluoromethoxy | 3-Chlorophenyl | 201 to 203 (HCl salt) |
| 5 | H | Cyclopropyl | Difluoromethoxy | 4-Chlorophenyl | 263 to 265 (1/2$H_2O$ adduct) |
| 6 | H | Cyclopropyl | Difluoromethoxy | 4-Fluorophenyl | 224 to 226 (HCl salt) |
| 7 | H | Cyclopropyl | Difluoromethoxy | 3-Methoxyphenyl | 209 to 212 |
| 8 | H | Cyclopropyl | Difluoromethoxy | 4-Methoxyphenyl | 253 to 255 |
| 9 | H | Cyclopropyl | Difluoromethoxy | 4-Nitrophenyl | 278 to 283 |
| 10 | H | Cyclopropyl | Difluoromethoxy | 4-Aminophenyl | 255 to 260 ($H_2O$ adduct) |

TABLE 21-continued

Structure: quinoline-3-carboxylic acid with Y at position 5, F at position 6, piperazinyl (N-R³) at position 7, R² at position 8, N-R¹ at position 1, and 4-oxo.

| Example | Y | R¹ | R² | R³ | m.p. (°C.) |
|---|---|---|---|---|---|
| 11 | H | Cyclopropyl | Difluoromethoxy | 4-Dimethylaminophenyl | 265 to 271 (decomposed) |
| 12 | H | Cyclopropyl | Difluoromethoxy | 4-Trifluoromethylphenyl | 224 to 226 (1/2H₂O adduct) |
| 13 | H | Cyclopropyl | Difluoromethoxy | 2-Pyridyl | 230 to 232 (HCl salt) |
| 14 | H | Cyclopropyl | Difluoromethoxy | 6-Methoxy-2-pyridyl | 209 to 212 (1/2H₂O adduct) |
| 15 | H | Cyclopropyl | Difluoromethoxy | 4-Amino-2-pyridyl | 238 to 244 (HCl salt.1/2H₂O adduct) |
| 16 | H | Cyclopropyl | Difluoromethoxy | 3-Ethylamino-2-pyridyl | 232 to 234 |
| 17 | H | Cyclopropyl | Difluoromethoxy | 3-Nitro-2-pyridyl | 233 to 237 |
| 18 | H | Cyclopropyl | Difluoromethoxy | 2-Pyrimidinyl | 264 to 266 |
| 19 | H | Cyclopropyl | Difluoromethoxy | 5-Chloro-2-pyrimidinyl | 258 to 260 (1/2H₂O adduct) |
| 20 | H | Cyclopropyl | Difluoromethoxy | 4,6-Dimethoxy-2-pyrimidinyl | 291 to 293 |
| 21 | H | Cyclopropyl | Difluoromethoxy | 2-Benzoxazolyl | 269 to 272 |
| 22 | Amino | Cyclopropyl | Difluoromethoxy | 2-Pyridyl | 288 to 290 (1/2H₂O adduct) |
| 23 | H | Methyl | Difluoromethoxy | 2-Methoxyphenyl | 238 to 239 (1/2H₂O adduct) |
| 24 | H | Methyl | Difluoromethoxy | 2-Pyrimidinyl | 272 to 274 |
| 25 | H | Isopropyl | Difluoromethoxy | 2-Methoxyphenyl | 192 to 196 |
| 26 | H | Isopropyl | Difluoromethoxy | 2-Pyrimidinyl | 278 to 281 (1/2H₂O adduct) |
| 27 | H | 2-Fluoroethyl | F | 2-Methoxyphenyl | 248 to 250 |
| 28 | H | Ethyl | Difluoromethoxy | 2-Methylphenyl | 262 to 264 |
| 29 | Amino | Isopropyl | Difluoromethoxy | 2-Methoxyphenyl | 232 to 233 |
| 30 | H | Ethyl | Difluoromethoxy | 2-Ethoxyphenyl | 186 to 188 |
| 31 | H | Ethyl | Difluoromethoxy | 2-Thiazolyl | 242 to 244 |
| 32 | H | Ethyl | Difluoromethoxy | 2-Pyridyl | 251 to 253 |
| 33 | H | Ethyl | Difluoromethoxy | 3-Nitro-2-pyridyl | 218 to 219 (HCl salt.1/2H₂O adduct) |
| 34 | H | Ethyl | Difluoromethoxy | 5-Chloro-2-pyrimidinyl | 285 to 288 |
| 35 | H | Ethyl | Difluoromethoxy | 6-Ethyl-2-pyrimidinyl | 197 to 201 |
| 36 | H | Ethyl | Difluoromethoxy | 6-Chloro-4-pyrimidinyl | 224 to 226 |
| 37 | H | Ethyl | Difluoromethoxy | 2-Pyrazinyl | 257 to 260 |
| 38 | H | 2-Fluoroethyl | Difluoromethoxy | 2-Methoxyphenyl | 230 to 231 |
| 39 | H | 2-Fluoroethyl | Difluoromethoxy | 2-Pyrimidinyl | 264 to 266 |
| 40 | H | Methyl | Difluoromethoxy | 3-Methoxyphenyl | 171 to 172 |
| 41 | H | Methyl | Difluoromethoxy | 4-Methoxyphenyl | 255 to 257 |
| 42 | H | Methyl | Difluoromethoxy | 4-Fluorophenyl | 270 to 272 |
| 43 | H | Methyl | Difluoromethoxy | 2-Pyridyl | 254 to 255 |
| 44 | H | H | Difluoromethoxy | 2-Methoxyphenyl | 254 to 256 |

TABLE 21-continued

[Structure: quinolone core with Y, F at positions, R³-N-piperazine-N at 7, R² at 8, R¹ on N, COOH at 3]

| Example | Y | R¹ | R² | R³ | m.p. (°C.) |
|---|---|---|---|---|---|
| 45 | H | 2-Hydroxyethyl | Difluoromethoxy | 2-Methoxyphenyl | 237 to 241 |
| 46 | H | 2-Acetoxyethyl | Difluoromethoxy | 2-Methoxyphenyl | 209 to 211 |
| 47 | H | Carboxymethyl | Difluoromethoxy | 2-Methoxyphenyl | 231 to 232 |
| 48 | H | 2-Dimethylaminoethyl | Difluoromethoxy | 2-Methoxyphenyl | 236 to 237 |
| 49 | H | 2-Morpholinoethyl | Difluoromethoxy | 2-Methoxyphenyl | 215 to 217 |
| 50 | H | 2-Pyridylmethyl | Difluoromethoxy | 2-Methoxyphenyl | 237 to 239 |
| 51 | H | Methylamino | Difluoromethoxy | 2-Methoxyphenyl | 234 to 236 |
| 52 | H | 2-Hydroxyethyl | Difluoromethoxy | 2-Pyrimidinyl | 254 to 256 |
| 53 | H | Methylamino | Difluoromethoxy | 2-Pyrimidinyl | 231 to 233 |
| 54 | H | 2-Hydroxyethyl | F | 2-Pyrimidinyl | 239 to 241 |
| 55 | H | Ethyl | Cl | 2-Pyrimidinyl | 230 to 231 (1/2H₂O adduct) |
| 56 | F | Cyclopropyl | F | 2-Pyrimidinyl | 255 to 257 |
| 57 | H | 2-Propenyl | Difluoromethoxy | 2-Pyrimidinyl | 255 to 256 (1/2H₂O adduct) |
| 58 | H | 2-Propynyl | Difluoromethoxy | 2-Pyrimidinyl | 254 to 255 |
| 59 | H | Ethyl | Methyl | 2-Pyrimidinyl | 270 to 272 (1/2H₂O adduct) |
| 60 | H | 2,4-Difluorophenyl | Difluoromethoxy | 2-Pyrimidinyl | 188 to 190 |
| 61 | Methyl | Ethyl | H | 2-Methoxyphenyl | 242 to 243 |
| 62 | H | Ethyl | Difluoromethoxy | 4-Pyrimidinyl | 238 to 240 |

Example 63

Synthesis of 1-ethyl-6-fluoro-8-difluoromethoxy-7-[4-(2-methoxyphenyl)piperazin-1-yl] -1,4-dihydro-4-oxoquinoline-3carboxylic acid

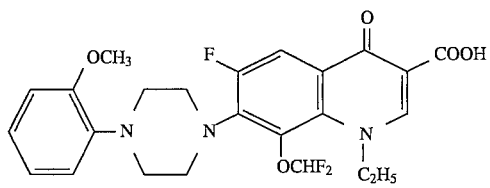

To a suspension of 5.0 g (0.016 mole) of 1-ethyl-6,7-difluoro-8-difluoromethoxy-1,4-dihydro -4-oxoquinoline-3-carboxylic acid and 20 ml of methyl isobutyl ketone was added 4.54 g (0.032 mole) of boron trifluoride.diethyl ether complex and the mixture was refluxed by heating for 6 hours while stirring. The reaction mixture was left to stand for cooling and, precipitated crystals were collected by filtration and washed with ether and chloroform to obtain 32 g of 1-ethyl-6,7-difluoro-8-difluoromethoxy-1,4-dihydro-4-oxoquinoline-3-carboxylic acid.BF₂ chelate compound as pale pink crystals.

To 5 ml of dimethyl sulfoxide were added 0.5 g (0.00136 mole) of the thus obtained chelate compound, 1.3 g (0.0068 mole) of 1-(2-methoxyphenyl)piperazine and 2 ml of triethylamine, and the mixture was stirred at room temperature for 5 hours and then left to stand overnight. Water was added to the reaction mixture, and the yellow crystals which precipitated were collected by filtration and washed with water. The crystals were dissolved in 100 ml of 80% methanol containing 2.5 ml of triethylamine, and the solution was refluxed by heating for 12 hours. Then, the solvent was removed under reduced pressure, and the residue was washed with a mixed solvent of ethanol and water, and dried to obtain 0.5 g of the title compound as a pale red powder.

Melting point: 219° to 222° C.

NMR(DMSO-d₆, δ): 1.28 (3H, t, J=7.0Hz), 3.11 (4H, br.s), 3.47 (4H, br. s), 3.81 (3H, s) , 4.74 (2H, q, J=7.0 Hz), 6.92 ~ 7.32 (5H, m), 8.01 ~ 8.04 (1H, d, J=12.1Hz), 8.96 (1H, s)

MS spectrum (CI): m/e 4 92 (M⁺+1)

Examples 64 to 89

By the same method as in Example 63, compounds shown in Table 22 and Table 23 were synthesized.

TABLE 22

| Example | $R^1$ | $R^2$ | $R^3$ | n | m.p. (°C.) |
|---|---|---|---|---|---|
| 64 | Cyclopropyl | Methoxy | 2-Methoxyphenyl | 1 | 201 to 203 ($H_2O$ adduct) |
| 65 | Cyclopropyl | Methoxy | 2-Pyridyl | 1 | 209 to 213 (HCl salt.$H_2O$ adduct) |
| 66 | Cyclopropyl | Methoxy | 2-Pyrimidinyl | 1 | 262 to 264 |
| 67 | Ethyl | Difluoromethoxy | 2-Pyrimidinyl | 1 | 251 to 253 |
| 68 | Ethyl | Difluoromethoxy | 4-Methoxyphenyl | 1 | 247 to 249 |
| 69 | Ethyl | Methoxy | 2-Methoxyphenyl | 1 | 245 to 247 |
| 70 | 2-Fluoroethyl | Methoxy | 2-Methoxyphenyl | 1 | 239 to 241 |
| 71 | Cyclopropyl | F | 2-Methoxyphenyl | 1 | 207 to 209 |
| 72 | Cyclopropyl | H | 2-Methoxyphenyl | 1 | 227 to 229 (½$H_2O$ adduct) |
| 73 | Cyclopropyl | F | 2-Pyridyl | 1 | 238 to 241 (HCl salt) |
| 74 | Ethyl | F | 2-Methoxyphenyl | 1 | 221 to 223 (½$H_2O$ adduct) |
| 75 | Ethyl | H | 2-Methoxyphenyl | 1 | 208 to 209 (¼$H_2O$ adduct) |
| 76 | 4-Fluorophenyl | H | 2-Pyridyl | 1 | >300 |
| 77 | Cyclopropyl | Difluoromethoxy | 2-Pyrimidinyl | 2 | 279 to 282 |
| 78 | Ethyl | Ethoxy | 2-Methoxyphenyl | 1 | 223 to 225 |
| 79 | Ethyl | Difluoromethoxy | 2-Pyrimidinyl | 2 | 246 to 248 |
| 80 | Cyclopropyl | H | 2-Pyrimidinyl | 1 | 296 to 298 (½$H_2O$ adduct) |
| 81 | 2,4-Difluorophenyl | H | 2-Pyrimidinyl | 1 | >300 (½$H_2O$ adduct) |
| 82 | 2-Fluoroethyl | F | 2-Pyrimidinyl | 1 | 260 to 262 |
| 83 | Ethyl | Difluoromethoxy | 2-Pyrimidinyl | 1 | 252 to 255 (HCl salt) |

TABLE 23

| Example | A | G | $R^3$ | m.p. (°C.) |
|---|---|---|---|---|
| 84 | —$CH_3$ | >CH— | 2-Methoxyphenyl | 262 to 264 |
| 85 | —$CH_3$ | >CH— | 2-Pyridyl | 267 to 272 1/2$H_2O$ adduct) |
| 86 | —$CH_2F$ | >CH— | 2-Pyridyl | 272 to 273 (decomposed) (HCl salt.$H_2O$ adduct) |
| 87 | —$CH_2F$ | >CH— | 2-Pyrimidinyl | 290 to 299 |
| 88 | —H | >CH— | 2-Pyrimidinyl | 289 to 298 (decomposed) (HCl salt.$H_2O$ adduct) |
| 89 | —$CH_3$ | >N— | 2-Pyrimidinyl | >300 |

Example 90

Synthesis of 6-fluoro-1-(4-fluorophenyl)-7-[4-(2-methoxyphenyl)piperazin-1-yl]-1,4-dihydro-4-oxo-1,8-naphthyridine-3-carboxylic acid

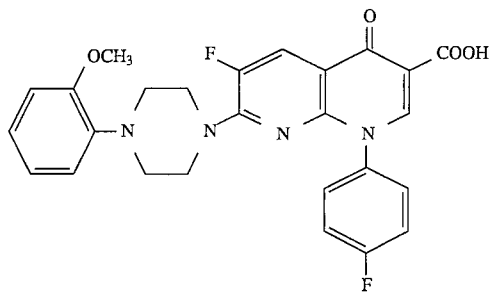

In 40 ml of ethanol was dissolved 0.81 g (0.0042 mole) of 1-(2-methoxyphenyl)piperazine, and to the solution was added gradually 1.02 g (0.0028 mole) of ethyl 7-chloro-6-fluoro-1-(4-fluorophenyl)-1,4-dihydro-4-oxo-1,8-naphthyridine-3-carboxylate at 30° C. while stirring. After completion of the addition, the mixture was reacted at the same temperature for 4 hours. After the reaction mixture was cooled, crystals precipitated were collected by filtration and washed with ethanol. To the crystals were added 12 ml of a 6N hydrochloric acid aqueous solution, and the mixture was refluxed by heating for 6 hours. After cooling, the reaction mixture was adjusted to pH 8.5 with a 1N sodium hydroxide aqueous solution, and crystals precipitated were collected by filtration and applied to silica gel column chromatography (the eluent used was a mixture of chloroform methanol =9.5:0.5) to obtain 0.87 g of the title compound as slightly yellow powder.

Melting point: 272° to 273° C.

NMR (DMSO-$d_6$, δ): 2.97 (4H, br. s), 3.71 (4H, br. s), 3.80 (3H, s), 6.86 ~ 7.70 (8H, m), 8.17 ~ 8.20 (1H, d, J=13.6Hz), 8.70 (1H, s), 15.13 (1H, s)

MS spectrum (CI): m/e 493 ($M^+$+1)

Examples 91 to 93

By the same method as in Example 90, compounds shown in Table 24 were synthesized.

TABLE 24

| Example | $R^1$ | $R^3$ | m.p. (°C.) |
|---|---|---|---|
| 91 | Ethyl | 2-Methoxyphenyl | 218 to 220 |
| 92 | Ethyl | 2-Pyrimidinyl | 296 to 298 |
| 93 | 2,4-Difluorophenyl | 2-Pyrimidinyl | 271 to 272 |

Example 94

Synthesis of 1-ethyl-6-fluoro-8-difluoromethoxy-7-[3-methyl-4-(2-pyrimidinyl)piperazin-1-yl]-1,4-dihydro-4-oxoquinoline-3-carboxylic acid

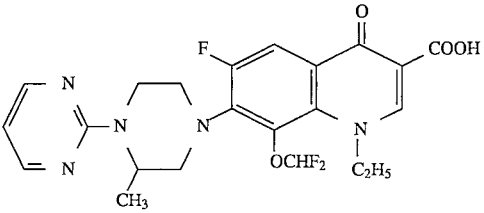

In 60 ml of pyridine were dissolved 3.19 g (0.01 mole) of 1-ethyl-6,7-difluoro-8-difluoromethoxy-1,4-dihydro-4-oxoquinoline-3-carboxylic acid and 3.0 g (0.03 mole) of 2methylpiperazine, and the mixture was stirred at 105° to 110° C. for 2 hours. Then, the solvent was removed under reduced pressure. Water was added to the residue, and crystals precipitated were collected by filtration, washed with water and ethanol, and dried to obtain 3.23 g of 1-ethyl-6-fluoro-8-difluoromethoxy-7-(3-methylpiperazin-1-Yl)-1,4-dihydro-4-oxoquinoline-3-carboxylic acid as pale yellow powder.

To 20 ml of N,N-dimethylformamide were added 1.6 g (0.004 mole) of the powder, 0.9 g (0.008 mole) of 2-chloropyrimidine and 0.81 g (0.008 mole) of triethylamine, and the mixture was stirred at 130° C. for 15 hours. Then, the solvent was removed under reduced pressure. Ethanol was added to the residue, and crystals precipitated were collected by filtration and applied to silica gel column chromatography (the eluent used was a mixture of chloroform methanol =9.5 : 0.5) to obtain 0.34 g of the title compound as pale yellow powder.

Melting point: 219° to 221° C.

MS spectrum (CI): m/e 478 ($M^+$+1)

Elemental analysis (%): in terms of $C_{22}H_{22}F_3N_5O_4$
Calculated: C: 55.35, H: 4.64, N: 14.67
Found: C: 55.41, H: 4.56, N: 14.65

Examples 95 and 97

Using a similar method to Example 94, but using appropriate starting materials, the compounds shown in Table 25 were synthesized.

TABLE 25

| Example | $R^1$ | $R^2$ | $R^3$ | $R^4$ | m.p. (°C.) |
|---|---|---|---|---|---|
| 95 | t-Butyl | H | 2-Pyrimidinyl | H | 276 to 278 |
| 96 | Ethyl | Difluoromethoxy | 2-Pyrimidinyl | H | 252 to 254 |

(The compound is the same compound as that of Example 67 but prepared by a different method.)

| 97 | Cyclopropyl | Methoxy | 2-Pyrimidinyl | Methyl | 235 to 237 |

Example 98

Synthesis of 1-ethyl-6-fluoro-8-difluoromethoxy-7-[4-(2-pyrimidinyl)piperazin-1-yl]-3 -(5-tetrazolyl)-1,4-dihydro-4-oxoquinoline

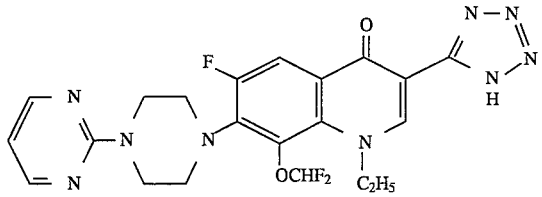

In the same manner as in Example 1, 4.85 g of 3-cyano-1-ethyl-6,7-difluoro-8-difluoromethoxy -1,4-dihydro-4-oxoquinoline and 9.49 g of 1-(2-pyrimidinyl)piperazine to obtain 4.2 g of 3-cyano-1-ethyl-6-fluoro-8-difluoromethoxy-7-[4-(2-pyrimidinyl)piperazin-1-yl ]-1,4-dihydro-4-oxoquinoline as a pale yellow powder.

Melting point: 286° to 290° C. (decomposed)

To 25 ml of xylene were added 0.5 g (0.0011 mole) of 3-cyano-1-ethyl-6-fluoro-8-difluoromethoxy -7-[4-(2-pyrimidinyl) piperazin-1-yl] -1,4-dihydro-4-oxoquinoline obtained as described above, 0.21 g of (0.0033 mole) of sodium azide and 1.07 g (0.0033 mole) of tributyltin chloride, and the mixture was stirred under reflux by heating for 9 hours. After the mixture was cooled to room temperature, 7 ml of a 1N hydrochloric acid aqueous solution was added thereto, and the mixture was stirred. Then, crystals precipitated were collected by filtration, washed with ethanol and toluene, and applied to silica gel column chromatography (the eluent used was a mixture of chloroform: methanol =9 :1) to obtain 0.37 g of the title compound as pale yellow powder.

Melting point: 265° to 268° C.

MS spectrum (CI): m/e 488 (M$^+$+1)

Elemental analysis (%): in terms of $C_{21}H_{20}F_3N_9O_2 \cdot \frac{1}{2}H_2O$ Calculated: C: 50.81, H: 4.06, N: 25.39

Found: C: 50.96, H: 4.16, N: 25.58

Example 99

Synthesis of 1-ethyl-8-difluoromethoxy-7-[4-(2-pyrimidinyl)piperazin-1-yl]-1,4-dihydro-4 -oxoquinoline-3-carboxylic acid

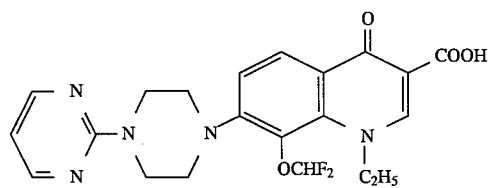

The same reaction as in Example 1 was carried out by using 1-ethyl-7-fluoro-8-difluoromethoxy-1,4-dihydro-4-oxoquinoline-3-carboxylic acid and 1-(2-pyrimidinyl)piperazine to obtain the title compound as white powder.

Melting point: >300° C.

MS spectrum (CI): m/e 446 (M$^+$+1)

Elemental analysis (%): in terms of $C_{21}H_{21}F_2N_5O_4$

Calculated: C: 56.63, H: 4.75, N: 15.72

Found: C: 56.70, H: 4.62, N: 15.34

Example 100

Synthesis of 6-fluoro-1-methyl-4-oxo-7-[4-(2-pyrimidinyl)piperazin-1-yl]-1H, 4H- [1,3]thiazeto[3,2-a]quinoline-3-carboxylic acid

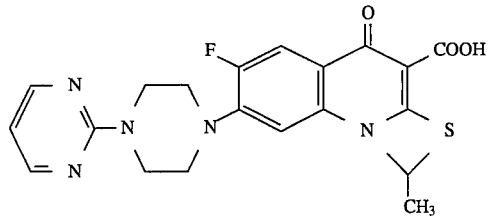

To 1 6 ml of N,N-dimethylformamide were added 2.0 g (0.0064 mole ) of ethyl 6, 7-difluoro-1-methyl-4-oxo-1H, 4H- [1,3] -thiazero[3,2-a]quinoline-3 -carboxylate, 3.0 g (0. 0129 mole) of 1 -(2-pyrimidinyl)piperazine dihydrochloride and 3.9 g (0.0256 mole) of 1,8-diazabicyclo [5.4.0]-7-undecene, and the mixture was stirred at room temperature for 5 days. The reaction mixture was added to water, and crystals precipitated were collected by filtration, washed with water and dried to obtain 2.8 g of ethyl 6-fluoro-1-methyl-4-oxo-7-[4-(2-pyrimidinyl) piperazin-1-yl ]-1H, 4H- [1,3]thiazeto [3,2-a] quinoline-3-carboxylate as pale yellow powder. To 0.8 g (0.0018 mole) of the powder were added 5 ml of methanol, 1 ml of dioxane, 1 ml of water and 7 ml of a 1N sodium hydroxide solution, and the mixture was stirred at room temperature for 3 days. The reaction mixture was adjusted to pH 7.2 by adding a diluted acetic acid aqueous solution, and crystals precipitated were collected by filtration and applied to silica gel column chromatography (the eluent used was a mixture of chloroform: methanol = 20:1) to obtain 0.22 g of the title compound as slightly yellow powder.

Melting point: 266° to 268° C. (decomposed)

MS spectrum (CI): m/e 428 (M$^+$+1)

Elemental analysis (%): in terms of $C_{20}H_{18}FN_5O_3S \cdot \frac{1}{2}H_2O$ Calculated: C: 55.04, H: 4.39, N: 16.05

Found: C: 54.85, H: 4.19, N: 15.92

Example 101

Synthesis of 1-ethyl-6-fluoro-8-difluoromethoxy-7-[(4-hydroxy-3-phenylamino)pyrrolidin-1 -yl]-1,4-dihydro-4-oxoquinoline-3-carboxylic acid

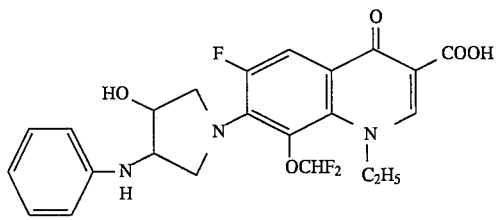

To 20 ml of pyridine were added 0.9 g (0.0028 mole) of 1-ethyl-6,7-difluoro-8-difluoromethoxy -1,4-dihydro-4-oxoquinoline-3-carboxylic acid, 1.52 g (0.0071 mole) of (4-hydroxy-3-phenylamino)pyrrolidine hydrochloride and 1.6 g (0.0142 mole) of triethylenediamine, and the mixture was stirred at room temperature for 30 minutes, followed by stirring at 105° to 110° C. for 3 hours. Then, the solvent was removed under reduced pressure. Water was added to the residue, and crystals precipitated were collected by filtration, washed with ethanol and applied to silica gel column chromatography (the eluent used was a mixture of chloroform: methanol =9.5 : 0.5) to obtain 0.71 g of the title compound as slightly yellowish white powder.

Melting point: 233° to 235° C.

MS spectrum (CI): m/e 478 (M$^+$+1)

Elemental analysis (%): in terms of $C_{23}H_{22}F_3N_3O_5$

Calculated: C: 57.86, H: 4.64, N: 8.80

Found: C: 57.83, H: 4.59, N: 8.80

Examples 102 and 103

Using a similar method to Example 101, but using appropriate starting materials, the compounds shown in Table 26 were synthesized.

TABLE 26

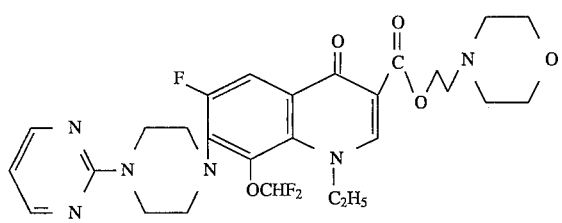

| Example | R$^1$ | R$^2$ | R$^6$ | R$^8$ | m.p. (°C.) |
|---|---|---|---|---|---|
| 102 | Ethyl | Difluoromethoxy | 2-Pyrimidinyl | H | 223 to 225 |
| 103 | Ethyl | Difluoromethoxy | Phenyl | Methoxy | 209 to 211 |

Example 104

Synthesis of 2-morpholinoethyl 1-ethyl-6-fluoro-8-difluoro-methoxy-7-[4-(2-pyrimidinyl)piperazin-1-yl]-1,4-dihydro-4-oxoquinoline-3-carboxylate

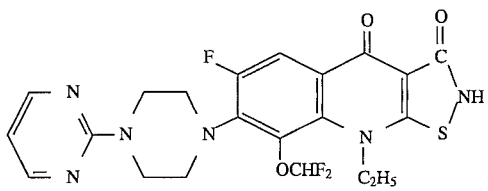

In 3 λ of methylene chloride were added 58.94 g (0.127 mole) of 1-ethyl-6-fluoro-8-difluoromethoxy-7-[4-(2-pyrimidinyl)piperazin-1-yl]-1,4-dihydro-4-oxoquinoline-3carboxylic acid, 25.05 g (0.191 mole) of 4-(2-hydroxyethyl-)morpholine, 23.3 g (0.191 mole) of 4-dimethylaminopyridine and 48.8 g (0.254 mole) of 1-ethyl-3-(3-dimethylaminopropyl)carbodiimide hydrochloride, and the mixture was stirred at room temperature for 4 days. Then, the solvent was removed under reduced pressure. The residue was dissolved in chloroform, washed with a 1N hydrochloric acid aqueous solution, washed with water and dried. The solvent was removed under reduced pressure, and the residue was applied to silica gel column chromatography (the eluent used was a mixture of chloroform: methanol : 28 % aqueous ammonia =40 : 9 : 1) to obtain 50.25 g of the title compound as slightly yellowish white powder.

Melting point: 162° to 164° C.

MS spectrum (CI): m/e 577 (M$^+$+1)

Elemental analysis (%): in terms of $C_{27}H_{31}F_3N_6O_5.\frac{1}{2}H_2O$

Calculated: C: 55.38, H: 5.34, N: 14.35

Found: C: 55.06, H: 5.20, N: 14.26

Examples 105 to 108

Using a similar method to Example 104, but using appropriate starting materials, the compounds shown in Table 27 were synthesized.

TABLE 27

| Example | R$^1$ | R$^3$ | Z | m.p. (°C.) |
|---|---|---|---|---|
| 105 | Ethyl | 2-Pyrimidinyl | Ethoxycarbonyl | 138 to 141 |
| 106 | Ethyl | 2-Pyrimidinyl | 2-Piperidinoethoxycarbonyl | 140 to 143 |
| 107 | Ethyl | 2-Pyrimidinyl | 2-(4-methylpiperidino)ethoxycarbonyl | 186 to 188 |
| 108 | Methyl | 2-Methoxyphenyl | 2-Morpholinoethoxycarbonyl | 192 to 193 |

Example 109

Synthesis of 9-ethyl-6-fluoro-8-difluoromethoxy-7-[4-(2-pyrimidinyl)piperazin-1-yl]-2,3,4,9-tetrahydroisothiazolo[5,4-b]quinolin-3,4-dione The same reaction as in Example 1 was carried out by using mg (1.44 mmole) of 9-ethyl-6,7-difluoro-8-difluoromethoxy-2,3,4,9-tetrahydroisothiazolo[5,4-b] quinolin-3, 4-dione and 1.9 g (11.5 mmole) of 1-(2-pyrimidinyl)piperazine to obtain 10 mg of the title compound as pale yellow powder.

Melting point: 259° to 262° C.

MS spectrum (CI): m/e 493 (M$^+$+1)

Elemental analysis (%): in terms of $C_{21}H_{19}F_3N_6O_3S.\frac{1}{2}H_2O$

Calculated: C: 50.30, H: 3.82, N: 16.75

Found: C: 50.56, H: 3.51, N: 17.03

Example 110

Anti-HIV Activity

Anti-HIV activity for the compounds of the present invention was assayed by the method of Pauwel, et al, [Pauwel, R., et al, J. Virological Methods (1988), 20, 309–321].

Exponentially growing MT-4 cells were centrifuged, and the pellets were resuspended in RPMI-1640 medium containing 10% fetal serum (serum medium). Portions of the cell suspension were either inoculated with HIV, or left uninfected. Serum medium was then further added to the suspensions, which were then washed and centrifuged. The resulting pellets were then suspended in serum medium to a concentration of $4 \times 10^5$ cells/ml. Preparations of the test compound (in serum medium) were deleted in a stepwise manner, and 100 µl of each of the solutions were placed in separated wells of a 96-well plastic microtitre plate. 100 µl of each of the cell suspensions (infected and non-infected) were then added to the wells, so that each dilution of each of the test compounds was tested against both infected and noninfected cells. Blanks (not added either of the cells) were also prepared. The preparations were then cultured by standing the plate at 37° C. for 5 days in the presence of 5 % carbon dioxide gas.

At the end of this time, living cells were assayed for CPE inhibitory activity by the spectrophotometric assay of the blue formazan produced by the reduction of MTT [3-(4,5-dimethylthiazol-2-yl) -2,5-diphenyl-tetrazolium bromide] which was added to the preparations.

CPE inhibitory activity was defined as 100% in non-infected cells to which no test compounds had been added, while CPE inhibitory activity was defined as 0% in infected cells to which test compounds had not been added. The effective concentration ($EC_{50}$) of the compound at which 50% CPE inhibition was observed in HIV infected cells was then determined. A second index was then generated, concerning cellular cytotoxic activity of the compounds, by calculating the concentration ($CC_{50}$) at which the test compounds caused 50% growth inhibition of non-infected cells.

Finally, a selective index (S.I.) was generated by calculating the value of $CC_{50}/EC_{50}$, to give an index of anti-HIV activity. The results are shown in Table 28.

Analysis of the preparations, at various stages, indicated that the cells and preparations consistently remained mycoplasma-free.

TABLE 28

| Compound of Example | $EC_{50}$ µg/ml | S.I. |
|---|---|---|
| 1 | 0.015 | 400 |
| 2 | 0.03 | 100 |
| 6 | 0.02 | 34 |
| 7 | 0.22 | 113 |
| 8 | 0.1 | 500 |
| 17 | 0.5 | 250 |
| 18 | 0.07 | 121 |
| 19 | 0.07 | 57 |
| 21 | 0.037 | 16 |
| 23 | 0.021 | 309 |
| 24 | 0.07 | 257 |
| 29 | 0.05 | 22 |
| 37 | 0.23 | >109 |
| 38 | 0.07 | 79 |
| 46 | 0.06 | 155 |
| 53 | 0.3 | >83 |
| 63 | 0.01 | 1000 |
| 67 (96) | 0.08 | >500 |
| 70 | 0.5 | 20 |
| 85 | 1.0 | 17 |
| 87 | 0.074 | >512 |
| 92 | 0.8 | 31 |
| 94 | 0.5 | 21 |
| 95 | 0.4 | >62 |
| 99 | 1.0 | >25 |
| 100 | 0.4 | 9 |

As can be seen from the above Table, the compounds of the present invention are effective in very small doses, and also exhibit an extremely high selective index.

By contrast, the prior art compounds (shown in Tables 29 and 30 below), and which are known as antibacterials, all had an $EC_{50}$ in excess of 100 µg/ml, when tested as above. Thus, the known compounds are at least 100 times less effective than the compounds of the present invention as anti-HIV agents.

TABLE 29

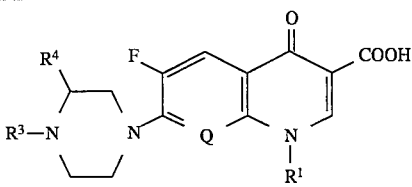

| General name | Q | $R^1$ | $R^3$ | $R^4$ |
|---|---|---|---|---|
| Enoxacin | =N— | Ethyl | H | H |
| Ciprofloxacin | =CH— | Cyclopropyl | H | H |
| Norfloxacin | =CH— | Ethyl | H | H |
| Ofloxacin | =C—O—CH$_2$—CH(CH$_3$)— | | Methyl | H |
| DR-3355 | =C—O—CH$_2$—CH(CH$_3$)— (s) | | Methyl | H |
| Lomefloxacin | =CF— | Ethyl | H | Methyl |
| Fleroxacin | =CF— | 2-Fluoroethyl | Methyl | H |
| Difloxacin | =CH— | 4-Fluorophenyl | Methyl | H |

TABLE 30

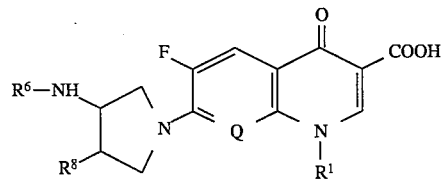

| General name | $R^1$ | Q | $R^6$ | $R^8$ |
|---|---|---|---|---|
| Tosufloxacin | 2,4-Difluorophenyl | =N— | H | H |

Reference example 1

Synthesis of 6,7-difluoro-8-difluoromethoxy-1-(2-pyridylmethyl)-1,4-dihydro-4-oxoquinoline-3 -carboxylic acid

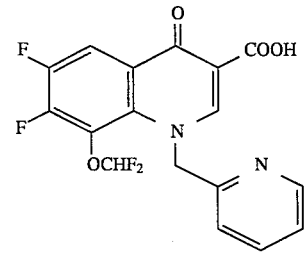

In 37 ml of toluene was dissolved 30 g (0.124 mole) of 2,4,5-trifluoro-3-difluoromethoxybenzoic acid, and 35 ml of thionyl chloride and 0.5 ml of N,N-dimethylformamide were added thereto. The mixture was refluxed by heating for 4 hours. After the reaction, toluene and excess thionyl chloride were removed under reduced pressure to obtain 2,4,5-trifluoro-3-difluoromethoxybenzoyl chloride.

Separately, 15.5 g (0.135 mole) of magnesium ethoxide and 20.9 g (0.130 mole) of diethyl malonate were refluxed by heating in 100 ml of anhydrous tetrahydrofuran for 2.5 hours under stirring to obtain a tetrahydrofuran suspension of diethyl ethoxy magnesium malonate. To the suspension was added dropwise a solution of the above acid chloride dissolved in 20 ml of tetrahydrofuran at room temperature under stirring, and the mixture was further stirred at room temperature for 2 hours. To the reaction mixture was added 100 ml of 1N hydrochloric acid, and the mixture was stirred vigorously. The mixture was separated, and the organic layer was washed with water and dried over anhydrous sodium sulfate. Then, the solvent was removed under reduced pressure to obtain 51.8 g of diethyl 2,4,5-trifluoro-3-difluoromethoxybenzoylmalonate as pale red liquid.

MS spectrum (CI): m/e 385 ($M^+$+1) m/e 339 ($M^+$-$OC_2H_5$)

Next, the liquid obtained was mixed with 200 ml of dioxane, and 23.6 g (0.124 mole) of p-toluenesulfonic acid.monohydrate was added thereto. The mixture was refluxed by heating for 8.5 hours. The reaction mixture was concentrated under reduced pressure, to the residue were added water and 10.41 g (0.124 mole) of sodium hydrogen carbonate, and the mixture was extracted with ethyl acetate. The ethyl acetate layer was washed with water, dried over anhydrous sodium sulfate and then concentrated under reduced pressure to obtain 32.0 g of ethyl 2,4,5-trifluoro-3-difluoromethoxybenzoylacetate as yellow liquid.

MS spectrum (CI): m/e 313 ($M^+$+1) m/e 225 (M+-$CH_2COOC_2H_5$)

To 4.85 g (0.0155 mole) of ethyl 2,4,5-trifluoro-3-difluoromethoxybenzoylacetate obtained as described above were added 11 ml of acetic anhydride and 3.2 ml of triethyl orthoformate, and the mixture was refluxed by heating for 2 hours. Then, excess acetic anhydride and triethyl orthoformate were removed under reduced pressure. The residue was dissolved in 150 ml of dichloromethane, and to the solution was added dropwise 2.01 g (0.0186 mole) of 2-aminomethylpyridine under ice cooling and stirring. The mixture was stirred under ice cooling for 1 hour. The reaction mixture was concentrated under reduced pressure, and the residue was applied to silica gel column chromatography (the eluent used was a mixture of toluene : ethyl acetate =9: 1) to obtain 6.56 g of ethyl 2-(2,4,5-trifluoro-3-difluoromethoxybenzoyl)-3 -(2-pyridylmethylamino)acrylate as amber liquid. Recrystallization was carried out by using n-hexane to obtain 3.6 g of white crystals.

MS spectrum (CI): m/e 431 ($M^+$+1)

In 50 ml of N,N-dimethylformamide was dissolved 5.6 g (0. 013 mole) of ethyl 2- (2,4,5-trifluoro-3-difluoromethoxybenzoyl)-3- (2-pyridylmethylamino) acrylate, and 2.2 g (0,026 mole) of sodium hydrogen carbonate was added thereto. The mixture was stirred at 120° C. for 30 minutes. Then, the reaction mixture was poured into 200 ml of water, and crystals precipitated were collected by filtration. The collected crystals were washed with water and ethanol and driedtoobtain2.6gofethyl6,7-difluoro-8-difluoromethoxy-1-(2-pyridylmethyl)-1,4-dihydro-4-oxoquinoline-3carboxylate as yellow crystals.

MS spectrum (CI): m/e 411 ($M^+$+1)

Next, 1.7 g (0.0041 mole) of the ester compound was suspended in a mixed solution of 4.2 ml of acetic acid, 1.5 ml of water and 0.48 ml of conc. sulfuric acid, and the suspension was refluxed by heating for 2 hours under stirring. After the suspension was cooled to room temperature, water was added thereto and insolubles were collected by filtration. The insolubles collected by filtration were washed with water and dried to obtain 1.1 g of 6,7-difluoro-8-difluoromethoxy-1-(2-pyridylmethyl)-1,4-dihydro -4-oxoquinoline-3-carboxylic acid as white crystals.

Melting point: 207° to 213° C. (decomposed)

MS spectrum (CI): m/e 383 ($M^+$+1)

Reference examples 2 to 9

In the same manner as in Reference example 1, compounds shown in Table 31 were synthesized.

TABLE 31

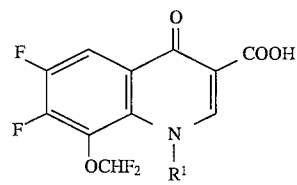

| Reference example | $R^1$ | Physical properties | | |
|---|---|---|---|---|
| | | MS spectrum (CI) | m.p. | Shape |
| 2 | H | m/e 292($M^+$ + 1) 247($M^+$ − $CO_2$) | 275 to 277° C. | White crystal |
| 3 | —$CH_2CH_2OH$ | m/e 336($M^+$ + 1) 291($M^+$ − $CO_2$) | 176 to 177° C. | White powder |
| 4 | —$CH_2CH$=$CH_2$ | m/e 332($M^+$ + 1) 288($M^+$ − $CO_2$) | 149 to 151° C. | White crystal |
| 5 | —$CH_2C$≡CH | m/e 330($M^+$ + 1) 285($M^+$ − $CO_2$) | 168 to 169° C. | White crystal |
| 6 | 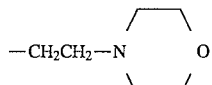 | m/e 405($M^+$ + 1) | 161 to 167° C. | Slightly yellow powder |

TABLE 31-continued

[Structure: quinoline with F at 6, F at 7, OCHF2 at 8, N-R1, COOH at 3, =O at 4]

| Reference example | R¹ | MS spectrum (CI) | m.p. | Shape |
|---|---|---|---|---|
| 7 | —CH₂CH₂—N(CH₃)₂ | m/e 363(M⁺ + 1) | 186 to 188° C. | White powder |
| 8 | —CH₂CH₂—O—CO—CH₃ | m/e 378(M⁺ + 1) 333(M⁺ − CO₂) | 115.5 to 116.5° C. | White powder |
| 9 | —CH₂—CO—O—CH₃ | m/e 364 (M⁺ + 1) | 187 to 189° C. | Slightly yellow powder |

Reference example 10

Synthesis of 1-ethyl-7-fluoro-8-difluoromethoxy-1,4-dihydro-4-oxoquinoline-3-carboxylic acid

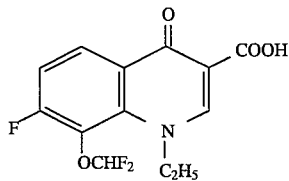

In 290 ml of acetic acid were dissolved 26.4 g (0.168 mole) of 2-fluoro-6-nitrophenol and 17.2 g (0.168 mole) of acetic anhydride, and 3.0 g of 5 % palladium carbon was added thereto. Hydrogen gas was passed through the mixture, with stirring, at room temperature for 2 hours. After the reaction mixture had been filtered and the filtrate concentrated under reduced pressure, the residue was extracted with ethyl acetate. The ethyl acetate layer was washed with water and dried over anhydrous sodium sulfate. The solvent was removed under reduced pressure, and the residue was applied to silica gel column chromatography (the eluent used was a mixture of ethyl acetate : toluene =1 : 2) to obtain 25.9 g of 2-acetylamino-6-fluorophenol as brown crystals.

MS spectrum (CI): m/e 170 (M⁺+1) m/e 127 (M⁺+1-COCH₃)

In 110 ml of N,N-dimethylformamide was dissolved 25.9 g (0.153 mole) of 2-acetylamino-6-fluorophenol obtained as described above, and 25.4 g (0.184 mole) of potassium carbonate and 33.1 g (0.383 mole) of chlorodifluoromethane were added thereto. The mixture was stirred in an autoclave at 100° C. for 5 hours. After completion of the reaction, the reaction mixture was poured into 1 λ of water and extracted with ethyl acetate. The ethyl acetate layer was washed with water and dried over anhydrous sodium sulfate. Then, the solvent was removed under reduced pressure, and the residue was applied to silica gel column chromatography (the eluent used was a mixture of ethyl acetate : toluene = 1 : 3) to obtain 30.4 g of 3-fluoro-2-difluoromethoxyacetanilide as slightly brownish crystals.

MS spectrum (CI): m/e 220 (M⁺+1)

In 180 ml of ethyl alcohol was dissolved 30.3 g (0.138 mole) of 3-fluoro-2-difluoromethoxyacetanilide obtained as described above, and 50.3 ml of conc. hydrochloric acid was added thereto. The mixture was refluxed by heating for 3 hours. After completion of the reaction, ethyl alcohol and conc. hydrochloric acid were removed under reduced pressure, and 200 ml of water was added to the residue. The mixture was neutralized with potassium carbonate and then extracted with chloroform. The chloroform layer was washed with a saturated saline solution and dried over anhydrous sodium sulfate. Then, the solvent was removed under reduced pressure, and the residue was applied to silica gel column chromatography (the eluent used was chloroform) to obtain 22.4 g of 3-fluoro-2-difluoromethoxyaniline as red liquid.

A mixture of 22.4 g (0.127 mole) of 3-fluoro-2-difluoromethoxyaniline obtained as described above and 27.4 g (0.127 mole) of diethyl ethoxymethylenemalonate was heated at 120° C. for 5 hours. The mixture was cooled to room temperature, n-hexane was added thereto, and the mixture was filtered. Products collected by filtration was washed with n-hexane and dried to obtain 37.5 g of N-(2, 2-diethoxycarbonylvinyl)-3-fluoro-2-difluoromethoxyaniline as white powder.

A mixture of 10.0 g (0.029 mole) of N-(2,2-diethoxycarbonylvinyl)-3-fluoro-2-difluoromethoxyaniline obtained as described above and 70 ml of diphenyl ether was refluxed by heating for 30 minutes. The mixture was cooled to room temperature, and n-hexane was added thereto. Crystals precipitated were collected by filtration and dried to obtain 5.25 g of ethyl 7-fluoro-8-difluoromethoxy-4-hydroxyquinoline-3-carboxylate as white powder.

Melting point: 218° to 219° C.

MS spectrum (CI): m/e 302 (M⁺+1)

In 96 ml of N,N-dimethylformamide was dissolved 3.0 g (0.01 mole) of ethyl 7-fluoro-8-difluoromethoxy-4-hydroxyquinoline-3-carboxylate obtained as described above, and 6.9 g (0.05 mole) of potassium carbonate and 12.5 g (0.08 mole) of ethyl iodide were added thereto. The mixture was stirred at 100° C. for 14 hours. After completion of the reaction, the solvent was removed under reduced pressure, and water was added to the residue. Crystals precipitated were collected by filtration and applied to silica gel column chromatography (the eluent used was a mixture of chloroform: methanol =95 : 5) to obtain 1.1 g of ethyl 1-ethyl-7-fluoro-8-difluoromethoxy-1.4 -dihydro-4-oxoquinoline-3-carboxylate as white crystals.

Melting point: 214.5° to 215.5° C.

MS spectrum (CI): m/e 329 (M$^+$+1)

Next, 1.1 g (0.0033 mole) of the ester compound was suspended in a mixed solution of 9 ml of acetic acid, 6.6 ml of water and 1.2 ml of conc. sulfuric acid, and the suspension was refluxed by heating for 2 hours under stirring. After the suspension was cooled to room temperature, water was added thereto and insolubles were collected by filtration. The insolubles collected by filtration were washed with water and dried to obtain 0.85 g of 1-ethyl-7-fluoro-8-difluoromethoxy-1,4-dihydro-4-oxoquinoline -3-carboxylic acid as white crystals.

Melting point: 169° to 170° C.

MS spectrum (CI): m/e 302 (M$^+$+1)

Reference example 11

Synthesis of 3-cyano-1-ethyl-6,7-difluoro-8-difluoromethoxy-1,4-dihydro-4-oxoquinoline

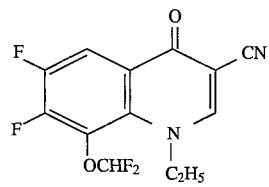

To 36.0 g (0.15 mole) of 2,4,5-trifluoro-3-difluoromethoxybenzoic acid were added 45 ml of toluene, 15 ml of thionyl chloride and 0.2 ml of N,N-dimethylformamide, and the mixture was refluxed by heating for 4 hours. After the reaction, toluene and excess thionyl chloride were removed under reduced pressure to obtain 2,4,5-trifluoro-3-difluoromethoxybenzoyl chloride.

In 75 ml of anhydrous tetrahydrofuran was dissolved 15.2 g (0.158 mole) of 3-dimethylaminoacrylonitrile, and 16.7 g (0.165 mole) of triethylamine was added thereto. To the mixture was gradually added dropwise at room temperature a solution of the above acid chloride dissolved in 15 ml of anhydrous tetrahydrofuran. After completion of the dropwise addition, the mixture was refluxed by heating for one hour, cooled to room temperature and then filtered. To the filtrate were added 9.7 ml of triethylamine and 14.7 g (0.18 mole) of ethylamine hydrochloride, and the mixture was stirred at 40° C. for 2 hours. The mixture was cooled to room temperature and then filtered. The filtrate was concentrated under reduced pressure, and the residue was applied to silica gel column chromatography (the eluent used was a mixture of ethyl acetate: toluene =3 : 7) to obtain 39.3 g of 2-(2,4, 5-trifluoro-3-difluoromethoxybenzoyl)-3-ethylaminoacrylonitrile as red liquid. The product was dissolved in 700 ml of a mixed solution of anhydrous diethyl ether and tetrahydrofuran, and 4.9 g (0.123 mole) of a 60% sodium hydride-mineral oil was gradually added thereto under ice cooling. The mixture was stirred at the same temperature for one hour. By adding 120 ml of a 1N hydrochloric acid to the reaction mixture and stirring the mixture vigorously, the whole reaction mixture was made acidic. Crystals precipitated were collected by filtration, washed with water and then washed with diethyl ether to obtain 17.2 g of 3-cyano-1-ethyl-6,7-difluoro-8-difluoromethoxy -1,4-dihydro-4-oxoquinoline as white powder.

Melting point: 194° to 195° C.

MS spectrum (CI): m/e 301(M$^+$+1)

Reference example 12

Synthesis of 1-(4,6-dimethoxy-2-pyrimidinyl) piperazine

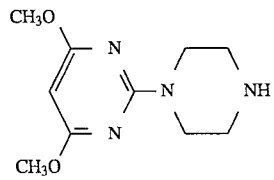

In 100 ml of acetonitrile was dissolved 10 g (0.0567 mole) of 1-benzylpiperazine, and 11.7 g (0.085 mole) of potassium carbonate and 14.8 g (0.068 mole) of 4,6-dimethoxy-2-methylsulfonylpyrimidine were added thereto. The mixture was refluxed by heating for 5 hours. The mixture was cooled to room temperature and then filtered. The filtrate was concentrated under reduced pressure, and the residue was applied to silica gel column chromatography (the eluent used was a mixture of ethyl acetate : toluene =1 : 9) to obtain 17.6 g of 4-(4,6-dimethoxy-2-pyrimidinyl)-1-benzylpiperazine as colorless liquid.

MS spectrum (CI): m/e 315 (M$^+$+1)

In 110 ml of ethanol was dissolved 3.9 g (0.0125 mole) of 4- ( 4,6-dimethoxy-2-pyrimidinyl)- 1-benzylpiperazine obtained as described above, and 2.5 g of 5% palladium carbon was added thereto. While refluxing the mixture under heating, hydrogen gas was passed for 6 hours. The reaction mixture was cooled to room temperature and then filtered. The filtrate was concentrated under reduced pressure, and the residue was applied to silica gel column chromatography (the eluent used was a mixture of chloroform: methanol =9 : 1) to obtain 1.38 g of 1-(4,6-dimethoxy-2-pyrimidinyl)piperazine as pale red crystals.

MS spectrum (CI): m/e 225 (M$^+$+1)

Reference example 13

Synthesis of 1-(6-methoxy-2-pyridyl)piperazine

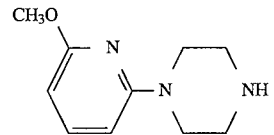

In a sealed tube, 8.6 g of piperazine and 2.9 g (0.02 mole) of 2-chloro-6-methoxypyridine were reacted at 150° C. for 4 hours. After the reaction, the reaction mixture was applied to silica gel column chromatography (the eluent used was a mixture of chloroform: methanol : 28% aqueous ammonia =40 : 9 : 1) to obtain 2.4 g of 1-(6-methoxy-2-pyridyl)piperazine as pale yellow liquid.

MS spectrum (CI): m/e 194 (M$^+$+1)

Reference example 14

Synthesis of 1-(2-thiazolyl)piperazine

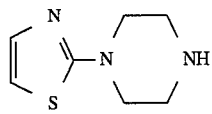

In 50 ml of acetonitrile was dissolved 5.0 g (0.0305 mole) of 2-bromothiazole, and 13.3 g (0.153 mole) of piperazine, 8.4 g (0.061 mole) of potassium carbonate and a catalytic amount of potassium iodide were added thereto. The mixture was refluxed by heating for 5 hours. The mixture was cooled to room temperature and then filtered. The filtrate was concentrated under reduced pressure, and the residue was applied to silica gel column chromatography (the eluent used was a mixture of chloroform: methanol : 28% aqueous ammonia =40 : 9 : 1) to obtain 3.62 g of 1-(2-thiazolyl)piperazine as colorless liquid.

MS spectrum (CI): m/e 170 ($M^+$+1)

Reference example 15

Synthesis of 1- (3-amino-2-pyridyl) piperazine

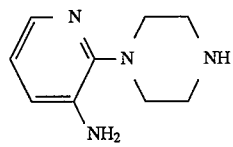

In 30 ml of methanol was dissolved 3.13 g (0.015 mole) of 1-(3-nitro-2-pyridyl)piperazine, and 2 g of 5% palladium carbon was added thereto. While stirring the mixture at room temperature, hydrogen gas was passed through for one hour. The reaction mixture was filtered, and the filtrate was concentrated under reduced pressure to obtain 2.56 g of 1-(3-amino-2-pyridyl)piperazine as pale yellow liquid.

MS spectrum (CI): m/e 179 ($M^+$+1)

Reference example 16

Synthesis of 1-(2-benzoxazolyl)piperazine

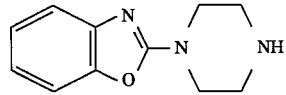

In 200 ml of acetonitrile were dissolved 33.6 g (0.39 mole) of piperazine and 10.0 g (0.065 mole) of 2-chlorobenzoxazole, and 9.0 g (0.065 mole) of potassium carbonate and a catalytic amount of potassium iodide were added thereto. The mixture was refluxed by heating for 11 hours under stirring. The mixture was cooled to room temperature and then filtered. The filtrate was concentrated under reduced pressure, and the residue was applied to silica gel column chromatography (the eluent used was a mixture of chloroform : methanol =9 : 1) to obtain 7.54 g of 1-(2-benzoxazolyl)piperazine as white crystals.

MS spectrum (CI): m/e 204 ($M^+$+1)

Reference example 17

Synthesis of 3-hydroxy-4-phenylaminopyrrolidine hydrochloride

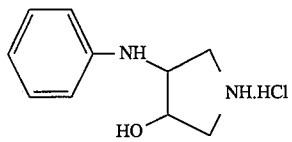

(1) In 20 ml of ethyl alcohol was dissolved 5 g (0.027 mole) of 1-t-butoxycarbonyl-3-epoxypyrrolidine, and 12.6 g (0.135 mole) of aniline was added thereto. The mixture was refluxed by heating for 20 hours. After the mixture was cooled to room temperature, the solvent was removed under reduced pressure, and the residue was applied to silica gel column chromatography (the eluent used was a mixture of ethyl acetate : toluene =1 : 4) to obtain 4.85 g of 1-t-butoxycarbonyl-3-hydroxy-4-phenylaminopyrrolidine as yellowish brown crystals.

MS spectrum (EI): m/e 278 ($M^+$) m/e 57 ($C_4H_9^+$)

(2) In 100 ml of methanol was dissolved 2.4 g (0.0086 mole) of 1-t-butoxycarbonyl-3-hydroxy-4-phenylaminopyrrolidine obtained as described above, and 30 ml of 6N hydrochloric acid was added thereto. After the mixture was refluxed by heating for 2.5 hours, the solvent was removed under reduced pressure. The resulting residue was washed with ethanol and ether to obtain 1.52 g of 3-hydroxy-4-phenylaminopyrrolidine hydrochloride as light brown powder.

MS spectrum (CI): m/e 179 ($M^+$+1)

Reference example 18

Synthesis of 3-methoxy-4-phenylaminopyrrolidine hydrochloride

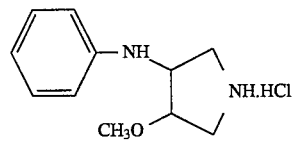

To 10 ml of anhydrous tetrahydrofuran was added 0.34 g (0.0085 mole) of a 60% sodium hydride-mineral oil, and while stirring the mixture at 45° to 50° C., 1.21 g (0.0085 mole) of methyl iodide was added thereto. To the mixture was added dropwise a solution of 2.37 g of 1-t-butoxycarbonyl-3-hydroxy-4-phenylaminopyrrolidine obtained in Reference example 17 (1) dissolved in 10 ml of anhydrous tetrahydrofuran, and the mixture was further stirred at the same temperature for 1 hour. After the mixture was cooled to room temperature, the solvent was removed under reduced pressure, and the residue was supplied to silica gel column chromatography (the eluent used was a mixture of methyl acetate: toluene =1 : 4) to obtain 1.98 g of 1-t-butoxycarbonyl-3-methoxy-4-phenylaminopyrrolidine as white crystals.

MS spectrum (CI): m/e 292 ($M^+$)

In 100 ml of methanol was dissolved 1.98 g (0.0068 mole) of 1-t-butoxycarbonyl-3-methoxy-4-phenylaminopyrrolidine obtained as described above, and 23.5 ml of 6N hydrochloric acid was added thereto. The mixture was left to stand at room temperature overnight. The solvent was removed under reduced pressure, and the residue was washed with ethanol to obtain 1.71 g of 3-methoxy-4-phenylaminopyrrolidine hydrochloride as white powder.

MS spectrum (CI): m/e 193 (M⁺+1)

Reference example 19

Synthesis of 1-(6-ethyl-4-pyrimidinyl)piperazine

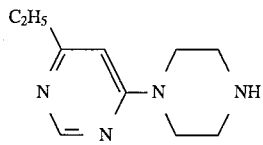

To 12.4 g (0.1 mole) of 6-ethyl-4-hydroxypyrimidine was added 50 ml of 1,2-dichloroethane, and 18.4 g (0.12 mole) of phosphorus oxychloride was added thereto. The mixture was refluxed by heating for 3 hours. After cooling, water was added to the reaction mixture, and the mixture was extracted with chloroform. The chloroform layer was washed with water and dried over anhydrous sodium sulfate. The solvent was removed under reduced pressure to obtain 10.38 g of 4-chloro-6-ethylpyrimidine as slightly red liquid.

Next, the liquid was mixed with 100 ml of acetonitrile, and to the solution were added 11.5 g (0.073 mole) of 1-ethoxycarbonylpiperazine, 20.2 g (0.146 mole) of potassium carbonate and a catalytic amount of potassium iodide. The mixture was refluxed by heating for 10 hours. The reaction mixture was cooled to room temperature and then filtered. The filtrate was concentrated under reduced pressure, and the residue was applied to silica gel column chromatography (the eluent used was a mixture of chloroform: methanol =4 : 1) to obtained 20.69 g of 1-(6-ethyl-4-pyrimidinyl)-4-ethoxycarbonylpiperazine as orange liquid.

MS spectrum (CI): m/e 265 (M⁺+1)

To 20.69 g (0.78 mole) of 1-(6-ethyl-4-pyrimidinyl)-4-ethoxycarbonylpiperazine obtained as described above was added 200 ml of 6N hydrochloric acid, and the mixture was refluxed by heating for 18 hours. The reaction mixture was adjusted to pH 10 or more by adding sodium hydroxide, and extracted with diethyl ether. The organic layer was dried over anhydrous sodium sulfate. The solvent was removed under reduced pressure, and the residue was applied to silica gel column chromatography (the eluent used was a mixture of chloroform: methanol =4 : 1) to obtain 1-(6-ethyl-4-pyrimidinyl)piperazine as colorless liquid.

MS spectrum (CI): m/e 193 (M⁺+1)

Reference example 20

Synthesis of 9-ethyl-6, 7-difluoro-8-difluoromethoxy-2,3,4,9-tetrahydroisothiazolo[5,4 -h]quinolin-3,4-dione

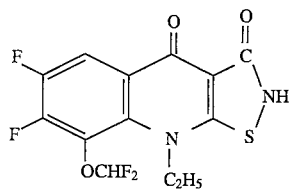

According to the method as described in Reference example 23 of Japanese Provisional Patent Publication No. 209367/1991, the reaction was carried out to obtain the title compound as a pale pink powder.

Melting point: 211° to 213° C.

MS spectrum (CI): m/e 349 (M⁺+1)

We claim:

1. A compound of formula (Ia) or pharmaceutically acceptable salt or ester thereof:

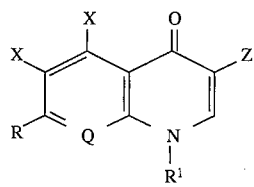

in which

X represents a hydrogen atom or a halogen atom;

Y represents a hydrogen atom, a halogen atom, a lower alkyl group, an unsubstituted amino group, or an amino group substituted by one or two groups selected from the group consisting of lower alkyl and aralkyl groups;

Z represents a protected or an unprotected carboxyl group or a 5-tetrazolyl group;

Q represents a group of formula (d):

where $R^2$ represents a hydrogen atom, a halogen atom, an unsubstituted lower alkoxy group, a lower alkoxy group substituted by one or more halogen atoms, an unsubstituted lower alkyl group, or a lower alkyl group substituted by one or more halogen atoms;

$R^1$ represents: a hydrogen atom; a lower alkenyl group which is unsubstituted or substituted by one or more halogen atoms; a lower alkenyl group; an amino group which as unsubstituted or substituted by one or more lower alkyl groups; a cycloalkyl group which is unsubstituted or substituted by at least one halogen atom; a lower alkoxy group; an aryl group which is unsubstituted or substituted by at least one substituent $R^0$ as defined below; a 5- or 6-membered aromatic heteromonocyclic group having one or two heteroatoms selected from the group consisting of N, O and S, said ring being unsubstituted or substituted by at least one substituent $R^0$ as defined below; a fused aromatic group which is a benzene ring fused with a 5- or 6-membered aromatic heteromono-cyclic group as defined above, said fused group being unsubstituted or substituted by at least one substituent $R^0$ as defined below; an unsubstituted lower alkyl group; or a lower alkyl group substituted by at least one substituent selected from the group consisting of halogen atoms, hydroxyl groups, carboxyl groups, alkanoyloxy groups, cycloalkyl groups, aryl groups which are unsubstituted or substituted by at least one substituent $R^0$ as defined below, 5- or 6-membered aromatic heteromonocyclic groups having one or two heteroatoms selected from the group consisting of N, O and S, said ring being unsubstituted or substituted by at least one substituent $R^0$ as defined below, fused aromatic groups as defined above, said fused group being unsubstituted or substituted by at least one substituent $R^0$ as defined below, or an amino group represented by the formula (e): as defined below, or an amino group represented by the formula (e):

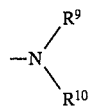

wherein $R^9$ and $R^{10}$ separately represent a hydrogen atom or a lower alkyl group, or $R^9$ and $R^{10}$, together with the nitrogen atom to which they are attached, form a 3- to 7-membered saturated monocyclic group comprising at least one further heteroatom selected from the group consisting of N, O and S, R represents a group of formula (h) or (i):

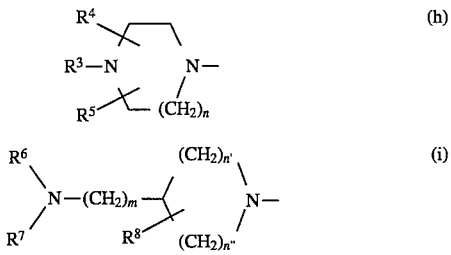

where $R^3$ and $R^6$ each represents an aryl group which is unsubstituted or substituted by at least one substituent $R^0$ as defined below; a 5- or 6-membered aromatic heteromonocyclic group having one or two heteroatoms selected from the group consisting of N, O and S, said ring being unsubstituted of substituted by at least one substituent $R^0$ as defined below; a fused aromatic group which is a benzene ring fused with a 5- or 6-membered aromatic heteromonocyclic group as defined above, said fused group being unsubstituted or substituted by at least one substituent $R^0$ as defined below;

$R^4$, $R^5$ and $R^7$ are the same or different, and each represents a hydrogen atom or a lower alkyl group;

$R^8$ represents a hydrogen atom, a lower alkyl group, a hydroxy group or a lower alkoxy group;

n = 1 or 2;

m = 0 or 1;

n' = 1 or 2; and n" = 1, 2, 3 or 4;

and substituent $R^0$ is selected from the group consisting of halogen atoms, nitro groups, hydroxy groups, lower alkyl groups which are unsubstituted or substituted with at least one halogen atom, lower alkoxy group, and amino groups which are unsubstituted or substituted with one or two lower alkyl groups, and when there are two or more substituents $R^0$, each are the same or different, provided that $R^0$ is not an unsubstituted or substituted amino group when $R^1$ is a phenyl group.

2. The compound according to claim 1, wherein $R^2$ is a lower alkoxy group which is unsubstituted or substituted by at least one halogen atom.

3. The compound according to claim 2, wherein $R^2$ is a methoxy group which is unsubstituted or substituted by at least one fluorine atom.

4. The compound according to claim 3, wherein $R^2$ is a difluoromethoxy group.

5. The compound according to claim 1, wherein X is a fluorine atom and Y is a hydrogen atom.

6. An anti-HIV composition comprising an effective anti-HIV amount of a compound according to claim 1 as an effective ingredient, together with a pharmaceutically acceptable carrier therefor.

7. A method of treating a patient suffering with AIDS comprising administering to the patient a pharmaceutically effective anti-HIV amount of the compound according to claim 1, or a pharmaceutically acceptable salt or ester thereof, either alone, or in admixture with a pharmaceutically acceptable carrier.

8. The compound according to claim 1, wherein said Z represents an unprotected carboxyl group or a carboxyl group protected by an unsubstituted $C_1$ to $C_4$ alkyl, aralkyl, $C_1$ to $C_4$ alkanoyloxyalkyl, $C_1$ to $C_4$ alkoxycarbonyloxyalkyl, N,N-dialkyl-substituted aminocarbonylalkyl, N,N-dialkyl-substituted aminoalkyl, alkyl substituted by a 5- or 6-membered saturated monocyclic group having one or two hetero atoms selected from the group consisting of N, O and S, 5-methyl-2-oxo-1,3-dioxolen-4-ylmethyl group or 5-phenyl-2-oxo-1,3-dioxolen-4-yl-methyl group.

9. The compound according to claim 1, wherein $R^2$ represents a hydrogen atom, a halogen atom or a lower alkyl group which is unsubstituted or substituted by at least one halogen atom.

10. The compound according to claim 1, wherein said $R^2$ represents a halogen atom, an unsubstituted lower alkoxy group, a lower alkoxy group substituted by one or more halogen atoms, an unsubstituted lower alkyl group or a lower alkyl group substituted by one or more halogen atoms.

11. The compound according to claim 1, wherein Z is a carboxyl group.

12. The compound according to claim 1, wherein said compound is selected from the group consisting of:

1-cyclopropyl-6-fluoro-8-difluoromethoxy-7-[4-(2-methoxyphenyl)piperazin-1-yl]-1,4 -dihydro-4-oxoquinoline-3-carboxylic acid, 1-cyclopropyl-6-fluoro-8-difluoromethoxy-7-(4-phenylpiperazin-1-yl)-1,4-dihydro-4 -oxoquinoline-3-carboxylic acid, 1-cyclopropyl-6-fluoro-8-difluoromethoxy-7-[4-(4-methoxyphenyl)piperazin-1-yl]-1,4 -dihydro-4-oxoquinoline-3carboxylic acid, 1-cyclopropyl-6-fluoro-8-difluoromethoxy-7-[4-(2-pyrimidinyl)piperazin-1-yl]-1,4 -dihydro-4-oxoquinoline-3-carboxylic acid, 6-fluoro-8-difluoromethoxy-1-methyl-7-[4-(2-methoxyphenyl)piperazin-1-yl]-1,4-dihydro -4-oxoquinoline-3-carboxylic acid, 6-fluoro-8-difluoromethoxy-1-methyl-7-[4-(2-pyrimidinyl)piperazin-1-yl]-1,4-dihydro -4-oxoquinoline-3-carboxylic acid, 1-(2-acetoxyethyl)-6-fluoro-8-difluoromethoxy-7-[4-(2-methoxyphenyl)piperazin-1-yl] -1,4-dihydro-4-oxoquinoline-3carboxylic acid, 1-ethyl-6-fluoro-8-difluoromethoxy-7-[4-(2-methoxyphenyl)piperazin-1-yl]-1,4-dihydro -4-oxoquinoline-3-carboxylic acid, 1-ethyl-6-fluoro-8-difluoromethoxy-7-[4-(2-pyrimidinyl) piperazin-1-yl]-1,4 -dihydro -4 -oxoquinoline-3-carboxylic acid, 2-morpholinoethyl 1-ethyl-6-fluoro-8-difluoromethoxy-7-[4-(2-pyrimidinyl)piperazin-1-yl]-1,4-dihydro-4-oxoquinoline-3-carboxylate, ethyl 1-ethyl-6-fluoro-8-difluoromethoxy-7-[4-(2-pyrimidinyl) piperazin-1-yl]-1,4 -dihydro-4-oxoquinoline-3-carboxylate, 2-piperidinoethyl 1-ethyl-6-fluoro-8-difluoromethoxy-7-[4-(2-pyrimidinyl)piperazin-1-yl]-1,4-dihydro-4-oxoquinoline-3-carboxylate, 2- (4-methylpiperidino) ethyl 1-ethyl-6-fluoro-8-difluoromethoxy-7-[4-(2-pyrimidinyl) piperazin-1-yl]-1,4-dihydro-4-oxoquinoline-3-carboxylate and 2-morpholinoethyl 6-fluoro-8-difluoromethoxy-1-methyl-7-[4-(2-methoxyphenyl)piperazin-1-yl]-1,4-dihydro-4-oxoquinoline-3-carboxylate.

13. The compound according to claim 1, wherein said R represents the group of formula (h) and $R^3$ represents either a 5- or 6-membered aromatic heteromonocyclic group containing one or two nitrogen atoms which is unsubstituted or substituted by $R^0$, or a fused group of said 5- or 6-membered aromatic heteromonocyclic group fused with a benzene ring which is unsubstituted or substituted by $R^0$.

14. The compound according to claim 1, wherein said R represents the group of formula (h) and $R^3$ represents an aromatic heteromonocyclic group which is unsubstituted or substituted by $R^0$.

15. The compound according to claim 1, wherein said R represents a group of formula (i) and $R^6$ represents either a 5- or 6-membered aromatic heteromonocyclic group containing one or two nitrogen atoms which is unsubstituted or substituted by $R^0$, or a fused group of said 5- or 6-membered aromatic heteromonocyclic group fused with a benzene ring which is unsubstituted or substituted by $R^0$.

16. The compound according to claim 1, wherein said R represents the group of formula (h).

17. The compound according to claim 1, wherein said R represents the group of formula (h) and $R^3$ represents an aromatic heterocyclic group.

18. The compound according to claim 1, wherein said R represents the group of formula (h) and $R^3$ represents an aromatic heteromonocyclic group.

19. The compound according to claim 1, wherein said R represents the group of formula (h) and $R^3$ represents a 5- or 6-membered aromatic heteromonocyclic group having one or two nitrogen atoms.

20. The compound according to claim 14, wherein $R^3$ is a pyridyl group, a pyrazinyl group or a pyrimidinyl group, and is unsubstituted or substituted by at least one substituent $R^0$.

21. The compound according to claim 20, wherein said R is 4-(2-pyrimidinyl)-piperazin-1-yl group.

22. The compound according to claim 1, wherein R is a group of the formula (h) and $R^3$ is a phenyl group which is unsubstituted or substituted by at least one substituent $R^0$.

23. The compound according to claim 1, wherein $R^1$ represents a hydrogen atom; an unsubstituted amino group; an amino group substituted by one or two lower alkyl groups; a cyclopropyl group; an unsubstituted lower alkyl group; or a lower alkyl group having a substituent selected from the group consisting of halogen, hydroxy, lower alkanoyloxy, mono- or di-lower alkyl-substituted amino, pyridyl and morpholino groups.

* * * * *

UNITED STATES PATENT AND TRADEMARK OFFICE
CERTIFICATE OF CORRECTION

PATENT NO. : 5,519,016

DATED : May 21, 1996

INVENTOR(S) : Tomio KIMURA et al.

It is certified that error appears in the above-indentified patent and that said Letters Patent is hereby corrected as shown below:

Column 28, line 5, replace "(V'-i)" with --(V'-1)--;

Column 29, lines 43 and 49, replace "Nos." with --No.--, respectively;

Column 42, line 18, replace "thiazero" with --thiazeto--;

Column 43, line 49, replace "3 λ" with --3 ℓ--;

Column 44, line 48, replace "using mg" with --using 500 mg--;

Column 45, line 8, replace "cells/mi" with --cells/ml--;

Column 48, line 19, replace "driedtoobtain2.6gofethyl6,7-difluoro" with --dried to obtain 2.6 g of ethyl 6,7-difluoro--;

Column 49, line 59, replace "1 λ" with --1 ℓ--;

Column 56, line 4 (Claim 1, Formula (Ia)), at 5-position of oxoquinoline ring, replace "X" with --Y--;

Column 56, line 36, replace "alkenyl" with --alkynyl--;

Column 56, line 37, replace "as" with --is--;

Column 56, line 49, replace "heteromono-cyclic" with --heteromonocyclic--;

UNITED STATES PATENT AND TRADEMARK OFFICE
CERTIFICATE OF CORRECTION

PATENT NO. : 5,519,016
DATED : May 21, 1996
INVENTOR(S) : Tomio KIMURA et al.

It is certified that error appears in the above-indentified patent and that said Letters Patent is hereby corrected as shown below:

Column 56, lines 66-67, delete "as defined below, or an amino group represented by the formula (e):";

Column 57, line 28, replace "of" with --or--;

Column 58, line 13, replace "5-methyl-2-oxo-1,3-dioxolen-4-yl-methyl" with --(5-methyl-2-oxo-1,3-dioxolen-4-yl)methyl--;

Column 58, lines 13-14, replace "5-phenyl-2-oxo-1,3-dioxolen-4-yl-methyl" with --(5-phenyl-2-oxo-1,3-dioxolen-4-yl)methyl--;

Column 58, line 48, replace "3carboxylic" with --3-carboxylic--.

Signed and Sealed this

Twenty-sixth Day of August, 1997

Attest:

BRUCE LEHMAN

*Attesting Officer*  *Commissioner of Patents and Trademarks*